(12) United States Patent
Hillman et al.

(10) Patent No.: US 6,281,334 B1
(45) Date of Patent: Aug. 28, 2001

(54) PROTEINS ASSOCIATED WITH APOPTOSIS

(75) Inventors: Jennifer L. Hillman, Mountain View; Henry Yue, Sunnyvale; Pretti Lal, Sunnyvale; Purvi Shah, Sunnyvale; Neil C. Corley, Mountain View, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/410,372

(22) Filed: Sep. 30, 1999

Related U.S. Application Data

(62) Division of application No. 08/985,335, filed on Dec. 4, 1997, now Pat. No. 6,080,847.

(51) Int. Cl.$^7$ .............................. C07K 1/00; C07K 14/00; C07K 17/00; C12Q 1/00; G01N 33/53

(52) U.S. Cl. ................................. 530/350; 435/4; 435/7.1

(58) Field of Search ................................. 530/350; 435/4, 435/7.1

(56) References Cited

U.S. PATENT DOCUMENTS 4,544,545 * 10/1985 Ryan et al. .

OTHER PUBLICATIONS

Hengartner, M.O. and H.R. Horvitz, "C. elegans Cell Survival Gene ced–9 Encodes a Functional Homolog of the Mammalian Proto–Oncogene bcl–2", *Cell*, 76:665–676 (1994).

Oltvai, Z.N. et al., "Bcl–2 Heterodimerizes In Vivo with a Conserved Homolog, Bax, That Accelerates Programed Cell Death", *Cell*, 74:609–619 (1993).

Yin, X.–M., et al., "BH1 and BH2 domains of Bcl–2 are required for inhibition of apoptosis and heterodimerization with Bax", *Nature*, 369:321–323 (1994).

Yang, E. et al., "Bad, a Heterodimeric Partner for Bcl–$X_L$ and Bcl–2, Displaces Bax and Promotes Cell Death", *Cell*, 80:285–291 (1995).

Kim, D. et al., "A cDNA encoding a putative 37 kDa leucine–rich repeat (LRR) protein, p37NB, isolated from S–type neuroblastoma cell has a differential tissue distribution", *Biochem. Biophys. Acta*, 1309:183–188 (1996).

Bengtsson, E. et al., "The Primary Structure of a Basic Leucine–rich Repeat Protein, PRELP, Found in Connective Tissues", *J. Biol. Chem.*, 270:25639–25644 (1995).

Shibahara, K. et al., "Isolation of a novel mouse gene MA–3 that is induced upon programmed cell death", *Gene*, 166:297–301 (1995) (GI 1384077; GI 1384078).

Onishi, Y. and H. Kizaki, "Molecular Cloning of the Genes Suppressed in RVC Lymphoma Cells by Topoisomerase Inhibitors", *Biochim. Biophys. Res. Commun.*, 228:7–13 (1996).

Yin, D.X. et al., (Direct Submission), GenBank Sequence Database (Accession 1683637), National Center for Biotechnology Information, National Library of Medicine, Bethesda, Maryland, 20894 (GI 1683636; GI 1683637) Nov. 23, 1996.

Yin, D.X. et al., (Direct Submission), GenBank Sequence Database (Accession U66879), National Center for Biotechnology Information, National Library of Medicine, Bethesda, Maryland, 20894 (GI 1683636; GI 1683637) Jan. 16, 1997.

Kim, D. et al., (Direct Submission), GenBank Sequence Database (Accession 1236329), National Center for Biotechnology Information, National Library of Medicine, Bethesda, Maryland, 20894 (GI 1236328; GI 1236329) Apr. 18, 1997.

Kim, D. et al., (Direct Submission), GenBank Sequence Database (Accession U32907), National Center for Biotechnology Information, National Library of Medicine, Bethesda, Maryland, 20894 (GI 1236328; GI 1236329) Apr. 18, 1997.

Shibahara, K. et al., (Direct Submission), GenBank Sequence Database (Accession 1384078), National Center for Biotechnology Information, National Library of Medicine, Bethesda, Maryland, 20894 (GI 1384077; GI 1384078) Jan. 10, 1999.

Shibahara, K. et al., (Direct Submission), GenBank Sequence Database (Accession D50465), National Center for Biotechnology Information, National Library of Medicine, Bethesda, Maryland, 20894 (GI 1384077; GI 1384078) Jan. 10, 1999.

Matsuhashi, S. et al., (Direct Submission), GenBank Sequence Database (Accession 1825562), National Center for Biotechnology Information, National Library of Medicine, Bethesda, Maryland, 20894 (GI 1825561; GI 1825562) Feb. 7, 1997.

Matsuhashi, S. et al., (Direct Submission), GenBank Sequence Database (Accession U83908), National Center for Biotechnology Information, National Library of Medicine, Bethesda, Maryland, 20894 (GI 1825561; GI 1825562) Feb. 7, 1997.

(List continued on next page.)

*Primary Examiner*—Sheela Huff
*Assistant Examiner*—Alana M. Harris
(74) *Attorney, Agent, or Firm*—Incyte Genomics, Inc.

(57) ABSTRACT

The invention provides three human proteins associated with cell proliferation, referred to collectively as "APOP" and individually as "APOP-1", "APOP-2", and "APOP-3", and polynucleotides which identify and encode APOP. The invention also provides expression vectors, host cells, agonists, antibodies and antagonists. The invention also provides methods for preventing and treating disorders associated with expression of APOP.

8 Claims, 27 Drawing Sheets

OTHER PUBLICATIONS

Wang, et al., "Bcl–2 Targets the Protein Kinase Raf–1 to Mitochondria", *Cell,* 87:629–638 (1996).

Adams, et al., "The Genome Directory", *Nature,* 377 (Suppl.) 3–174 (Sequence Comparison) (1995).

Kim, et al., "A cDNA encoding a putative 37 kDa leucine–rich repeat (LRR) protein, p37NB, isolated from S–type neuroblastoma cell has a differential tissue distribution", *Biochemica et Biophysica Acta,* 1309: 183–188 (1996).

Shibhara, et al., "Isolation of a novel mouse gene MA–3 that is induced upon programmed cell death", *Gene,* 166: 297–301 (1995).

Amino acid database, Accession #Q13288, 1996.*

Amino acid database, Accession #G02020, 1996.*

Lin et al. Structure–Function Relationships in Glucagon; Properties of Highly Purified Des–His(1)–, Monoiodo–, and [Des–Asn (28), Thr(29)] 9homoserine lactone (27))–glucagon. Biochemistry 14(8):1559–1563, 1975.*

Schwartz et al. A superactive insulin: [B1—Aspartic acid] insulin (human). Proc. Natl. Acad. Sci. USA 84:6408–6411, 1987.*

Biotechnology Industry Organization. Critical Synergy: The Biotechnology Industry and Intellectual Property Protection, 1994.*

Harlow E. and Lane D. Antibodies, A Laboratory Manual, 1988.*

* cited by examiner

```
                                                                                              54
        9        18        27        36        45
5' CGA CCG TCC GCG GGA GAC TGA GGT CCT GAG CCG ACA GCC TCA GCT CCC TGC CAG 63       72        81        90        99        108
GCC AGA CCC GGC AGA CAG ATG AGG GCC CAG GAG GCC TGG CGG GGG CGC 117      126       135       144       153       162
TAC GGT GGG AGA GGA AGC CAG GGG TAC CTG CCT CTG CCT TCC AGG GCC ACC GTT 171      180       189       198       207       216
GGC CCC AGC TGT GCC TTG ACT ACG TAA CAT CTT GTC CTC ACA GCC CAG AGC ATG
                                                                      M 225      234       243       252       261       270
TTC CAG ATC CCA GAG TTT GAG CCG AGT GAG CAG GAA GAC TCC AGC TCT GCA GAG
 F   Q   I   P   E   F   E   P   S   E   Q   E   D   S   S   S   A   E 279      288       297       306       315       324
AGG GGC CTG GGC CCC AGC CCC GCA GGG GAC GGG CCC TCA GGC TCC GGC AAG CAT
 R   G   L   G   P   S   P   A   G   D   G   P   S   G   S   G   K   H 333      342       351       360       369       378
CAT CGC CAG GCC CCA GGC CTC CTG TGG GAC GCC AGT CAC CAG GAG CAG CCA
 H   R   Q   A   P   G   L   L   W   D   A   S   H   Q   E   Q   P
```

```
     387                 396                 405                 414                 423                 432
     ACC AGC AGC         CAT GGA GGC         GCT GGG GCT         GTG GAG ATC         CGG AGT CGC         CAC
      T   S   S           H   G   G           A   G   A           V   E   I           R   S   R           H 441                 450                 459                 468                 477                 486
     AGC TCC TAC         CCC GCG ACG         GAG GAC GAA         ATG GGG ATG         GAG GAG CCC         AGC
      S   S   Y           P   A   T           E   D   E           M   G   M           E   E   P           S 495                 504                 513                 522                 531                 540
     CCC TTT CGG         GGC CGC TCG         GCG CCC CCC         AAC CTC TGG         GCA GCA CAG         CGC
      P   F   R           G   R   S           A   P   P           N   L   W           A   A   Q           R 549                 558                 567                 576                 585                 594
     TAT GGC CGC GAG CTC CGG AGG ATG AGT GAC GAG TTT GTG GAC TCC TTT AAG AAG
      Y   G   R   E   L   R   R   M   S   D   E   F   V   D   S   F   K   K 603                 612                 621                 630                 639                 648
     GGA CTT CCT CGC CCG AAG AGC GCG GGC ACA GCA ACG CAG ATG CGG CAA AGC TCC
      G   L   P   R   P   K   S   A   G   T   A   T   Q   M   R   Q   S   S 657                 666                 675                 684                 693                 702
     AGC TGG ACG CGA GTC TTC CAG TCC TGG GAT TGG CGG AAC TTG GGC AGG GGA AGC
      S   W   T   R   V   F   Q   S   W   D   W   R   N   L   G   R   G   S 711                 720
     TCC GCC CCC TCC CAG TGA CCT TCG CTC CAC ATC CCG AAA CTC CAC CCG TTC CCA
      S   A   P   S   Q
```

```
      765            774            783       792            801            810
CTG CCC TGG GCA GCC ATC TTG AAT ATG GGC GGA AGT ACT TCC CTC AGG CCT ATG 819            828            837       846            855            864
CAA AAA GAG GAT CCG TGC TGT CTC CTT TGG AGG GAG GGC TGA CCC AGA TTC CCT 873            882            891       900            909            918
TCC GGT GCG TGT GAA GCC ACG GAA GGC TTG GTC CCA TCG GAA GTT TTG GGT TTT 927            936            945       954            963            972
CCG CCC ACA GCC GCC GGA AGT GGC TCC GTG GCC CCG CCC TCA GGC TCC GGG CTT 981            990            999       1008           1017           1026
TCC CCC AGG CGC CTG CGC TAA GTC GCG AGC CAG GTT TAA CCG TTG CGT CAC CGG 1035           1044           1053      1062           1071           1080
GAC CCG AGC CCC CGC GAT GCC CTG GGG GCC GTG CTC ACT ACC AAA TGT TAA TAA 1089           1098
AGC CCG CGT CTG TGC AAA AAA AAA A 3'
```

```
                9              18              27        36              45          54
5' NGA ATG CAG CCC ATT CTC TGG AGA ACT TCC TCA CAC ACC GCA AAG AGA AGA 63              72              81        90              99         108
CTG AAA GAC AAA CCT GGG TGC AGC CAG AGA GGT CCA GAT AGA TGA GCT TGT GGC 117             126             135       144             153         162
ATC CAT TCC CCA AGT TCA GCC TAG GGA CTC CAC GTA CCC CAG CTG GGT CTC ATT 171             180             189       198             207         216
GTT CCA GAA CTG CAT TAG TTA AGA TTA CCC AGA CTT GGA TTT CAA AGG AAT ACT 225             234             243       252             261         270
TTC ATT GTT CCG TCT GTA ACA CGA AGT AAT TGG GGC CAG CTG GAT GTC AGG ATG
                                                                            M 279             288             297       306             315         324
CGT GTG GTT ACC ATT GTA ATC TTG CTC TGC TTT TGC AAA GCG GCT GAG CTG CGC
 R   V   V   T   I   V   I   L   L   C   F   C   K   A   A   E   L   R 333             342             351       360             369         378
AAA GCA AGC CCA GGC AGT GTG AGA AGC CGA GTG AAT CAT GGC CGG GCG GGT GGA
 K   A   S   P   G   S   V   R   S   R   V   N   H   G   R   A   G   G
```

FIGURE 4A

```
    387             396             405             414             423             432
GGC AGA GGC TCC AAC CCG GTC AAA CGC TAC GCA CCA GGC CTC CCG TGT GAC
 G   R   G   S   N   P   V   K   R   Y   A   P   G   L   P   C   D 441             450             459             468             477             486
GTG TAC ACA TAT CTC CAT GAG AAA TAC TTA GAT TGT CAA GAA AGA AAA TTA GTT
 V   Y   T   Y   L   H   E   K   Y   L   D   C   Q   E   R   K   L   V 495             504             513             522             531             540
TAT GTG CTG CCT GGT TGG CCT CAG GAT TTG CTG CAC ATG CTG CTA GCA AGA AAC
 Y   V   L   P   G   W   P   Q   D   L   L   H   M   L   L   A   R   N 549             558             567             576             585             594
AAG ATC CGC ACA TTG AAG AAC AAC ATG TTT TCC AAG TTT AAA AAG CTG AAA AGC
 K   I   R   T   L   K   N   N   M   F   S   K   F   K   K   L   K   S 603             612             621             630             639             648
CTG GAT CTG CAG CAG CAG AAT GAG ATC TCT AAA ATT GAG AGT GAG GCG TTC TTT GGT
 L   D   L   Q   Q   Q   N   E   I   S   K   I   E   S   E   A   F   F   G 657             666             675             684             693             702
TTA AAC AAA CTC ACC ACC CTC TTA CTG CAG CAC AAC CAG ATC AAA GTC TTG ACG
 L   N   K   L   T   T   L   L   L   Q   H   N   Q   I   K   V   L   T 711             720             729             738             747             756
GAG GAA GTG TTC ATT TAC ACA CCT CTC CTC TTG AGC TAC CTG CGT CTT TAT GAC AAC
 E   E   V   F   I   Y   T   P   L   L   S   Y   L   R   L   Y   D   N
```

FIGURE 4B

```
       765            774            783            792            801            810
CCC TGG CAC TGT ACT TGT GAG ATA GAA ACG CTT ATT TCA ATG TTG CAG ATT CCC
 P   W   H   C   T   C   E   I   E   T   L   I   S   M   L   Q   I   P 819            828            837            846            855            864
AGG AAC CGG AAT TTG GGG AAC TAC GCC AAG TGT GAA AGT CCA CAA GAA CAA AAA
 R   N   R   N   L   G   N   Y   A   K   C   E   S   P   Q   E   Q   K 873            882            891            900            909            918
AAT AAA AAA CTG CGG CAG ATA AAA TCT GAA CAG TTG TGT AAT GAA GAA AAG GAA
 N   K   K   L   R   Q   I   K   S   E   Q   L   C   N   E   E   K   E 927            936            945            954            963            972
CAA TTG GAC CCG AAA CCC CAA GTG TCA GGG AGA CCC CCA GTC ATC AAG CCT GAG
 Q   L   D   P   K   P   Q   V   S   G   R   P   P   V   I   K   P   E 981            990            999            1008           1017           1026
GTG GAC TCA ACT TTT TGC CAC AAT TAT GTG TTT CCC ATA CAA ACA CTG GAC TGC
 V   D   S   T   F   C   H   N   Y   V   F   P   I   Q   T   L   D   C 1035           1044           1053           1062           1071           1080
AAA AGG AAA GAG TTG AAA AAA GTG CCA AAC AAC ATC CCT CCA GAT ATT GTT AAA
 K   R   K   E   L   K   K   V   P   N   N   I   P   P   D   I   V   K 1089           1098           1107           1116           1125           1134
CTT GAC TTG TCA TAC AAT AAA ATC AAC CAA CTT CGA CCC AAG GAA TTT GAA GAT
 L   D   L   S   Y   N   K   I   N   Q   L   R   P   K   E   F   E   D
```

FIGURE 4C

```
            1143              1152              1161              1170              1179              1188
GTT CAT GAG CTG AAG AAA TTA AAC CTC AGC AGC AAT GGC ATT GAA TTC ATC GAT
 V   H   E   L   K   K   L   N   L   S   S   N   G   I   E   F   I   D 1197              1206              1215              1224              1233              1242
CCT GCC GCT TTT TTA GGG CTC ACA CAT TTA GAA GAA TTA GAT TCA AAC AAC
 P   A   A   F   L   G   L   T   H   L   E   E   L   D   S   N   N 1251              1260              1269              1278              1287              1296
AGT CTG CAA AAC TTT GAC TAT GGC GTA TTA GAA GAC TTG TAT TTT TTG AAA CTC
 S   L   Q   N   F   D   Y   G   V   L   E   D   L   Y   F   L   K   L 1305              1314              1323              1332              1341              1350
TTG TGG CTC AGA GAT AAC CCT TGG AGA TGT GAC TAC AAC ATT CAC TAC CTC TAC
 L   W   L   R   D   N   P   W   R   C   D   Y   N   I   H   Y   L   Y 1359              1368              1377              1386              1395              1404
TAC TGG TTA AAG CAC CAC TAC AAT GTC CAT TTT AAT GGC CTG GAA TGC AAA ACG
 Y   W   L   K   H   H   Y   N   V   H   F   N   G   L   E   C   K   T 1413              1422              1431              1440              1449              1458
CCT GAA GAA TAC AAA GGA TGG TCT GTG GGA AAA TAT ATT AGA AGT TAC TAT GAA
 P   E   E   Y   K   G   W   S   V   G   K   Y   I   R   S   Y   Y   E 1467              1476              1485              1494              1503              1512
GAA TGC CCC AAA GAC AAG TTA CCA GCA TAT CCT GAG TCA TTT GAC CAA GAC ACA
 E   C   P   K   D   K   L   P   A   Y   P   E   S   F   D   Q   D   T
```

FIGURE 4D

```
       1521            1530           1539           1548            1557          1566
GAA GAT GAT GAA TGG GAA AAA AAA AGA CAT AGA GAT CAC ACC GCA AAG AAG CAA AGC
 E   D   D   E   W   E   K   K   R   H   R   D   H   T   A   K   K   Q   S 1575            1584           1593           1602            1611          1620
GTA ATA ATT ACT ATA GTA GGA TAA GGT AGA AAT TGT TCT GAT TGT AAT TAG TTT
 V   I   I   T   I   V   G 1629            1638           1647           1656            1665          1674
TGT ATT TTC TAT ACT GGT GTT AGA AAA CAT ATG TTT ACA TTT GAT TAA CTG TGT 1683            1692           1701           1710            1719          1728
TGC CTA TTT ATG CAG GGT AAT CCA GCT AAA GGA AGC TTT CTT TAA TTA TAA GTA 1737            1746           1755           1764            1773          1782
TTA TTG TGA CTA TTA TAG TAA TCA AGA GAA TGC TAT CAT CCT GCT TGC CTG TCC 1791            1800           1809           1818            1827          1836
ATT TGT GGA ACA GCA TCT GGT GAT ATG CAA TTC CAC ACT GGT AAC CTG CAG CAG 1845            1854           1863           1872            1881          1890
TTG GGT CCT AAT GAT GGC ATT AGA CTT TCA TAA TGT CCT GTA TAA ATG TTT TTA
```

FIGURE 4E

```
      1899        1908        1917        1926        1935        1944
CTG CTT TTA GAA AAT AAA GAA AAA CTT GGT TCA TGT TTA CAT GCC TTT CGA 1953        1962        1971        1980        1989        1998
TAG CTG TTT GTG CAT ACT TAA AGA TGA TCA AAA TGA TTT TAT ACA AAT GCT GTT 2007        2016        2025        2034        2043        2052
ATA ATA AAA TGT CAT TCC CTA CCC CTC TAC TTT TTT TCA GTA AGT CAT CTT ATA 2061        2070        2079
CAT TAA ATA AAT TTC CAT TTC TGA AAA AAA A 3'
```

FIGURE 4F

| | | |
|---|---|---|
| 1 | M R V V T I V I L L C F C K A A E L R K A S P G S V R S R V N H G R A G G G R R | 1352286 |
| 1 | M R V V T I V I L L C F C K A A E L R K A S P G S V R S R V N H G R A G G G R R | GI 1236329 |
| 41 | G S N P V K R Y A P G L P C D V Y T Y L H E K Y L D C Q E R K L V Y V L P G W P | 1352286 |
| 41 | G S N P V K R Y A P G L P C D V Y T Y L H E K Y L D C Q E R K L V Y V L P G W P | GI 1236329 |
| 81 | Q D L L H M L L A R N K I R T L K N N M F S K F K K L K S L D L Q Q N E I S K I | 1352286 |
| 81 | Q D L L H M L L A R N K I R T L K N N M F S K F K K L K S L D L Q Q N E I S K I | GI 1236329 |
| 121 | E S E A F F G L N K L T T L L L Q H N Q I K V L T E E V F I Y T P L L S Y L R L | 1352286 |
| 121 | E S E A F F G L N K L T T L L L Q H N Q I K V L T E E V F I Y T P L L S Y L R L | GI 1236329 |
| 161 | Y D N P W H C T C E I E T L I S M L Q I P R N R N L G N Y A K C E S P Q E Q K N | 1352286 |
| 161 | Y D N P W H C T C E I E T L I S M L Q I P R N R N L A N Y A K C E S P Q E Q K N | GI 1236329 |
| 201 | K K L R Q I K S E Q L C N E E - K E Q L D P K P Q V S G R P P V I K P E V D S T | 1352286 |
| 201 | K K L R Q I K S E Q L C N E E E K E Q L D P K P Q V S G R P P V I K P E V D S T | GI 1236329 |
| 240 | F C H N Y V F P I Q T L D C K R K E L K K V P N N I P P D I V K L D L S Y N K I | 1352286 |
| 241 | F C H N Y V F P I Q T L D C K R K E L K K V P N N I P P D I V K L D L S Y N K I | GI 1236329 |

FIGURE 5A

```
280 NQLRPKEFEDVHELKKLNLSSNGIEFIDPAAFLGLTHLEE      1352286
281 NQLRPKEFEDVHELKKLNLSSNGIEFIDPGS-------        GI 1236329

320 LDLSNNSLQNFDYGVLEDLYFLKLLWLRDNPWRCDYNIHY      1352286
312 ----------------------------LR---------       GI 1236329

360 LYYWLKHHYNVHFNGLECKTPEEYKGWSVGKYIRSYYEEC      1352286
313 ---------------------------------------       GI 1236329

400 PKDKLPAYPESFDQDTEDDEWEKKHRDHTAKKQSVIITIV      1352286
313 ---------------------------------------       GI 1236329

```
                          9                18                27                36                45                54
5' NAC AGC TCG AGC TCG AGC CGC AAA ACT GTC TGC AGA CGT CAA TTT CGC CCC CCT 63                72                81                90                99               108
   CCC CCT TGT GAG AAC TCG CTA CGT AGC CAG CAA CTG TGT AGT GTC TAC AAA TGA 117               126               135               144               153               162
   TGA AAA CGA TCA GAA ATG CGA TTA GGT GTC GGG GAA AAA AGG GTT TCC CCT GTT 171               180               189               198               207               216
   TTT AAC TTG TAT TTT TAC TTT AAT TGT TAC AAT CTT GAT ATT CTT AAC GTG ACT 225               234               243               252               261               270
   TTT TTG GGA AAC CAC CAA GTG CTT TTT AAG CAA GGA GTT ACT GAT TCT GAA GGA 279               288               297               306               315               324
   AGA TTT CCA TTA GGT AAT TTG TTT AAT CAG TGC AAG CGA AAT TAA GGG AAA ATG
                                                                           M 333               342               351               360               369               378
   GAT GTA GAA AAT GAG CAG ATA CTG AAT GTA AAC CCT GCA GAT CCT GAT AAC TTA
   D   V   E   N   E   Q   I   L   N   V   N   P   A   D   P   D   N   L
```

FIGURE 7A

```
         387         396         405         414         423         432
AGT GAC TCT CTC TTT TCC GGT GAT GAA GAA AAT GCT GGG ACT GAG GAA GTA AAG
 S   D   S   L   F   S   G   D   E   E   N   A   G   T   E   E   V   K 441         450         459         468         477         486
AAT GAA ATA AAT GGA AAT TGG ATT TCA GCA TCC TCC ATT AAC GAA GCT AGA ATT
 N   E   I   N   G   N   W   I   S   A   S   S   I   N   E   A   R   I 495         504         513         522         531         540
AAT GCC AAG GCA AAA AGG CGA CTA AGG AAA AAC TCA TCC CGG GAC TCT GGC AGA
 N   A   K   A   K   R   R   L   R   K   N   S   S   R   D   S   G   R 549         558         567         576         585         594
GGC GAT TCG GTC AGC GAC AGT GGG AGT GAC GCC CTT AGA AGT GGA TTA ACT GTG
 G   D   S   V   S   D   S   G   S   D   A   L   R   S   G   L   T   V 603         612         621         630         639         648
CCA ACC AGT CCA AAG GGA AGG TTG CTG GAT AGG GCA GGA GGC AAA TCT GGG AAA GGA
 P   T   S   P   K   G   R   L   L   D   R   A   G   G   K   S   G   K   G 657         666         675         684         693         702
AGG GGA CTA CCA AAG AAA GGT GCA GGA GGC AAA GAT GTG TGG GGT ACA CCT
 R   G   L   P   K   K   G   A   G   G   K   D   V   W   G   T   P 711         720         729         738         747         756
GGA CAG GTG TAT GAT GTG GAG GAG GTG GAT GTG AAA GAT CCT AAC TAT GAT GAT
 G   Q   V   Y   D   V   E   E   V   D   V   K   D   P   N   Y   D   D

FIGURE 7B
```

```
      765             774             783             792             801             810
GAC CAG GAG AAC TGT GTT TAT GAA ACT GTA GTT TTG CCT GAT GAA AGG GCA
 D   Q   E   N   C   V   Y   E   T   V   V   L   P   D   E   R   A 819             828             837             846             855             864
TTT GAG AAG ACT TTA ACA CCA ATC ATA CAG GAA TAT TTT GAG CAT GGA GAT ACT
 F   E   K   T   L   T   P   I   I   Q   E   Y   F   E   H   G   D   T 873             882             891             900             909             918
AAT GAA GTT GCG GAA ATG TTA AGA GAT TTA AAT CTT GGT GAA ATG AAA AGT GGA
 N   E   V   A   E   M   L   R   D   L   N   L   G   E   M   K   S   G 927             936             945             954             963             972
GTA CCA GTG TTG GCA GTA TCC TTA GCA TTG GAG GGG AAG GCT AGT CAT AGA GAG
 V   P   V   L   A   V   S   L   A   L   E   G   K   A   S   H   R   E 981             990             999            1008            1017            1026
ATG ACA TCT AAG CTT CTT TCT GAC CTT TGT GGG ACA GTA ATG AGC ACA ACT GAT
 M   T   S   K   L   L   S   D   L   C   G   T   V   M   S   T   T   D 1035            1044            1053            1062            1071            1080
GTG GAA AAA TCA TTT GAT AAA TTG TTG AAA GAT CTA CCT GAA TTA GCA CTG GAT
 V   E   K   S   F   D   K   L   L   K   D   L   P   E   L   A   L   D 1089            1098            1107            1116            1125            1134
ACT CCT AGA GCA CCA CAG CTG GTG GGC CAG TTT ATT GCT AGA GCT GTT GGA GAT
 T   P   R   A   P   Q   L   V   G   Q   F   I   A   R   A   V   G   D
```

FIGURE 7C

```
       1143           1152           1161           1170           1179           1188
GGA ATT TTA TGT AAT ACC TAT ATT GAT AGT TAC AAA GGA ACT GTA GAT TGT GTG
 G   I   L   C   N   T   Y   I   D   S   Y   K   G   T   V   D   C   V 1197           1206           1215           1224           1233           1242
CAG GCT AGA GCT GCT CTG GAT AAG GCT ACC GTG CTT CTG AGT ATG TCT AAA GGT
 Q   A   R   A   A   L   D   K   A   T   V   L   L   S   M   S   K   G 1251           1260           1269           1278           1287           1296
GGA AAG CGT AGT AAA GAT AGT GTG TGG GGC TCT GGA GGT GGG CAG CAA TCT GTC AAT
 G   K   R   S   K   D   S   V   W   G   S   G   G   G   Q   Q   S   V   N 1305           1314           1323           1332           1341           1350
CAC CTT GTT AAA GAG ATT GAT ATG CTG AAA GAA TAT TTA CTC TCT GGA GAC
 H   L   V   K   E   I   D   M   L   K   E   Y   L   L   S   G   D 1359           1368           1377           1386           1395           1404
ATA TCT GAA GCT GAA CAT TGC CTT AAG GAA CTG GAA GTA CCT CAT TTT CAC CAT
 I   S   E   A   E   H   C   L   K   E   L   E   V   P   H   F   H   H 1413           1422           1431           1440           1449           1458
GAG CTT GTA TAT GAA GCT ATT ATA ATG GTT TTA GAG TCA ACT GGA GAA AGT ACA
 E   L   V   Y   E   A   I   I   M   V   L   E   S   T   G   E   S   T 1467           1476           1485           1494           1503           1512
TTT AAG ATG ATT TTG GAT TTA TTA AAG TCC CTT TGG AAG TCT TCT ACC ATT ACT
 F   K   M   I   L   D   L   L   K   S   L   W   K   S   S   T   I   T
```

FIGURE 7D

```
     1521        1530         1539        1548          1557        1566
GTA GAC CAA ATG AAA AGA GGT TAT GAG AGA ATT TAC AAT GAA ATT CCG GAC ATT
 V   D   Q   M   K   R   G   Y   E   R   I   Y   N   E   I   P   D   I 1575        1584         1593        1602          1611        1620
AAT CTG GAT GTC CCA CAT TCA TAC TCT GTG CTG GAG CGG TTT GTA GAA GAA TGT
 N   L   D   V   P   H   S   Y   S   V   L   E   R   F   V   E   E   C 1629        1638         1647        1656          1665        1674
TTT CAG GCT GGA ATA ATT TCC AAA CAA CTC AGA GAT CTT TGT CCT TCA AGG GGC
 F   Q   A   G   I   I   S   K   Q   L   R   D   L   C   P   S   R   G 1683        1692         1701        1710          1719        1728
AGA AAG CGT TTT GTA AGC GAA GGA GAT GGA GGT CGT CTT AAA CCA GAG AGC TAC
 R   K   R   F   V   S   E   G   D   G   G   R   L   K   P   E   S   Y 1737        1746         1755        1764          1773        1782
TGA ATA TAA GAA CTC TTG CAG TCT TAG ATG TTA TAA AAA TAT ATA TCT GAA TTG 1791        1800         1809        1818          1827        1836
TAA GAG TTG TTA GCA CAA GTT TTT TTT TTT TTT TAA GCA CTT GTT TTG 1845        1854         1863        1872          1881        1890
GGT ACA AGG CAT TTC TGA CAT TTT ATA AAC CTA CAT TTA AGG GGA ATT TTT AAA
```

FIGURE 7E

```
     1899         1908         1917         1926         1935         1944
GGA AAT GTT TTT TCT TTT TTT TTT GTT TTT CGA GGG GGC AAG GAG GGA CAG AAA 1953         1962         1971         1980         1989         1998
AGT AAC CTC TTC TTA AGT GGA ATA TTC TAA TAA GCT ACC TTT TGT AAG TGC CAT 2007         2016         2025         2034         2043         2052
GTT TAT TAT CTA ATC ATT CCA AGT TTT GCA TTG ATG TCT GAC TGC CAC TCC TTT 2061         2070         2079         2088         2097         2106
CTT TCA AGG ACA GTG TTT TTT GTA GTA AAA TCA CTG GTT TAT ACA AAG CTT TAT 2115         2124         2133         2142         2151         2160
TTA GGG GGT AAA GTT AAG CTG CTA AAA CCC CAT GTT GGC TGC TGC TGT TGA GAT 2169         2178         2187         2196         2205         2214
ACT GTG CTT TGG GAG TAA AAA AAG AAA GTT ATT TCT TTG TCT TAA AGA ATT TTT 2223         2232         2241         2250         2259         2268
AAA AAA TTA GTC ATG AGA CTT ATT CAT CTT TCC AGG GAA CAT ACT GAT TGG TCT
```

FIGURE 7F

```
                      2277        2286         2295         2304         2313         2322
              TAA AAG ACT AGA CAG TTA AGT AAA AGG TGG CTG GAA CAT CTA TTT TTC TAC AAA
                  2331          2340         2349         2358         2367         2376
              ACT GGA AAA ATG AAC CTG GTT CTA GAA GAA TGT ACA CCA AAA TAA AAC ATG TGA
                  2385          2394
              AGC AGT ATT GAA AAA AAA AA 3'
```

PROTEINS ASSOCIATED WITH APOPTOSIS

This application is a divisional application of U.S. application serial No. 08/985,335, filed Dec. 4, 1997, now U.S. Pat. No. 6,080,847.

FIELD OF THE INVENTION

This invention relates to nucleic acid and amino acid sequences of three human proteins associated with cell proliferation and to the use of these sequences in the diagnosis. prevention, and treatment of disorders associated with abnormal cell proliferation and apoptosis.

BACKGROUND OF THE INVENTION

Differentiation, growth, and function of eukaryotic cells are coordinated with various mechanisms which regulate DNA replication and prevent excessive proliferation. While uncoordinated cell proliferation can cause cancer, autoimmune diseases, and inflammatory diseases, programmed cell death or apoptosis removes excessive or damaged cells without causing tissue destruction and inflammatory response. A plethora of genes, named oncogenes, have been identified with cancer. Several highly conserved processes have been shown to regulate apoptosis.

bcl-2 proto-oncogene is a repressor of apoptosis and functions downstream in the regulation of cell-death processes. The C. elegans homolog of Bcl-2, CED-9, represses the apoptosis of 131 cells during the nematode development (Hengartner, M. O. and Horvitz, H. R. (1994) Cell 76: 665–676). Several Bcl-2-related proteins, such as Bax, Bcl-$X_L$, and Bad, share homology with Bcl-2 mostly within two conserved regions, named BH1 and BH2. Bcl-$X_L$ and Bcl-2 are shown to repress apoptosis, while Bax and Bad promote apoptosis. Specifically, Bax is capable of dimerizing with Bcl-2 and Bcl-$X_L$, whereas Bad is able to dimerize with Bcl-$X_L$ but not with Bcl-2. When Bax dimerizes with Bcl-2, the apoptosis-inhibiting function of Bcl-2 is suppressed (Oltvai, Z. N. et al. (1993) Cell 74: 609–619; Yin, X.-M. et al. (1994) Nature 369: 321–323). Similarly, when Bad displaces Bax and dimerizes with BCl-$X_L$, the apoptosis-repressive activity of Bcl-$X_L$ is inhibited (Yang, E. et al. (1995) Cell 80: 285–291).

Leucine-rich repeat (LRR) is a structural motif of about 20 to 29 amino acid residues in length associated with protein-protein interactions. The motif contains leucine or other aliphatic residues at positions 2, 5, 7, 12, 16, 21, and 24 and asparagine, cysteine or threonine at position 10. X-ray structure determination of LRR motifs suggests that each LRR is composed of a β-sheet and an α-helix.

p37NB is a 37 kDa LRR protein identified in human neuroblastoma cells (Kim, D. et al. (1996) Biochim. Biophys. Acta 1309: 183–188). Northern blot hybridization and RT-PCR studies show that p37NB is differentially expressed in several neuroblastoma cell lines. A related LRR protein, PRELP, is characterized as a 42 kDa secreted protein (Bengtsson, E. et al. (1995) J. Biol. Chem. 270: 25639–25644). PRELP consists of 10 LRR motifs ranging in length from 20 to 26 residues with asparagine at position 10. Northern analysis shows differential expression of PRELP in various tissues.

MA-3 or TIS is a mouse protein associated with apoptosis (Shibahara, K. et al. (1995) Gene 166: 297–301; Onishi, Y. and Kizaki, H. (1996) Biochim. Biophys. Res. Commun. 228: 7–13). The nucleotide sequence of the mouse proteins predicts an amino acid sequence of 469 residues. MA-3 is highly expressed in thymus and is present in all apoptosis-inducible cell lines including thymocytes, T cells, B cells, and pheochromocytoma (Shibahara et al, supra). TIS expression is down-regulated in the RVC lymphoma cells incubated with an topoisomerase I inhibitor, an antitumor drug, and the low expression level of TIS may be a contributing factor to the cytotoxicity of the topoisomerase inhibitors (Onishi and Kizaki, supra).

The discovery of three new human proteins associated with cell proliferation and the polynucleotides encoding them satisfies a need in the art by providing new compositions which are useful in the diagnosis, prevention, and treatment of disorders associated with abnormal cell proliferation and apoptosis.

SUMMARY OF THE INVENTION

The invention features three substantially purified polypeptides, proteins associated with cell proliferation, referred to collectively as "APOP" and individually as "APOP-1", "APOP-2", and "APOP-3." In one aspect, the invention provides a substantially purified polypeptide, APOP, comprising an amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5.

The invention further provides a substantially purified variant of APOP having at least 90% amino acid identity to the amino acid sequences of SEQ ID NO: 1, SEQ ID NO:3, or SEQ ID NO:5, or to a fragment of either of these sequences. The invention also provides an isolated and purified polynucleotide sequence encoding the polypeptide comprising an amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5. The invention also includes an isolated and purified polynucleotide variant having at least 90% polynucleotide identity to the polynucleotide sequence encoding the polypeptide comprising an amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5.

Additionally, the invention provides a composition comprising a polynucleotide sequence encoding the polypeptide comprising the amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5. The invention further provides an isolated and purified polynucleotide sequence which hybridizes under stringent conditions to the polynucleotide sequence encoding the polypeptide comprising an amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5, as well as an isolated and purified polynucleotide sequence which is complementary to the polynucleotide sequence encoding the polypeptide comprising the amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5.

The invention also provides an isolated and purified polynucleotide sequence comprising a polynucleotide sequence selected from the group consisting of SEQ ID NO:2, SEQ ID NO:4, SEQ ID NO:6, a fragment of SEQ ID NO:2, a fragment of SEQ ID NO:4, and a fragment of SEQ ID NO:6. The invention further provides an isolated and purified polynucleotide variant having at least 90% polynucleotide identity to the polynucleotide sequence comprising a polynucleotide sequence selected from the group consisting of SEQ ID NO:2, SEQ ID NO:4, SEQ ID NO:6, a fragment of SEQ ID NO:2, a fragment of SEQ ID NO:4, and a fragment of SEQ ID NO:6, as well as an isolated and purified polynucleotide sequence which is complementary to the polynucleotide sequence comprising a polynucleotide sequence selected from the group consisting of SEQ ID NO:2, SEQ ID NO:4, SEQ ID NO:6, a fragment of SEQ ID NO:2, a fragment of SEQ ID NO:4, and a fragment of SEQ ID NO:6.

The invention further provides an expression vector containing at least a fragment of the polynucleotide sequence encoding the polypeptide comprising an amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5. In another aspect, the expression vector is contained within a host cell.

The invention also provides a method for producing a polypeptide comprising the amino acid sequence of SEQ ID NO: 1, SEQ ID NO:3, SEQ ID NO:5, a fragment of SEQ ID NO: 1, a fragment of SEQ ID NO:3, or a fragment of SEQ ID NO:5, the method comprising the steps of: (a) culturing the host cell containing an expression vector containing at least a fragment of a polynucleotide sequence encoding APOP under conditions suitable for the expression of the polypeptide; and (b) recovering the polypeptide from the host cell culture.

The invention also provides a pharmaceutical composition comprising a substantially purified APOP having the amino acid sequence of SEQ I) NO: 1, SEQ ID NO:3, SEQ ID NO:5, a fragment of SEQ ID NO: 1, a fragment of SEQ ID NO:3, or a fragment of SEQ ID NO:5 in conjunction with a suitable pharmaceutical carrier.

The invention further includes a purified antibody which binds to a polypeptide comprising the amino acid sequence of SEQ ID NO: 1, SEQ ID NO:3, SEQ ID NO:5, a fragment of SEQ ID NO: 1, a fragment of SEQ ID NO:3, or a fragment of SEQ ID NO:5, as well as a purified agonist and a purified antagonist to the polypeptide.

The invention also provides a method for preventing or treating a cancer comprising administering to a subject in need of such treatment an effective amount of a pharmaceutical composition comprising purified APOP.

The invention also provides a method for preventing or treating a disorder associated with an increase in apoptosis comprising administering to a subject in need of such treatment an effective amount of a pharmaceutical composition comprising purified APOP.

The invention also provides a method for preventing or treating a cancer comprising administering to a subject in need of such treatment an effective amount of an antagonist of APOP.

The invention also provides a method for preventing or treating an inflammation comprising administering to a subject in need of such treatment an effective amount of an antagonist of APOP.

The invention also provides a method for preventing or treating a disorder associated with an increase in apoptosis comprising administering to a subject in need of such treatment an effective amount of an antagonist of APOP.

The invention also provides a method for detecting a polynucleotide encoding APOP in a biological sample containing nucleic acids, the method comprising the steps of: (a) hybridizing the complement of the polynucleotide sequence encoding the polypeptide comprising SEQ ID NO:1, SEQ ID NO:3, SEQ ID NO:5, a fragment of SEQ ID NO:1 , a fragment of SEQ ID NO:3, or a fragment of SEQ ID NO:5 to at least one of the nucleic acids of the biological sample, thereby forming a hybridization complex; and (b) detecting the hybridization complex, wherein the presence of the hybridization complex correlates with the presence of a polynucleotide encoding APOP in the biological sample. In one aspect, the nucleic acids of the biological sample are amplified by the polymerase chain reaction prior to the hybridizing step.

BRIEF DESCRIPTION OF THE FIGURES

FIGS. 1A, 1B, and 1C show the amino acid sequence (SEQ ID NO:1 ) and nucleic acid sequence (SEQ ID NO:2) of APOP-1 . The alignment was produced using MacDNASIS PRO™ software (Hitachi Software Engineering Co. Ltd. San Bruno, Calif.).

FIG. 2 shows the amino acid sequence alignments between APOP-1 (358637; SEQ ID NO: 1) and a human Bcl-2 binding component 6 (GI 1683637; SEQ ID NO:7), produced using the multisequence alignment program of DNASTAR™ software (DNASTAR Inc, Madison Wis.).

FIGS. 4A, 4B, 4C, 4D, 4E, and 4F show the amino acid sequence (SEQ ID NO:3) and nucleic acid sequence (SEQ ID NO:4) of APOP-2. The alignment was produced using MacDNASIS PRO™ software (Hitachi Software Engineering Co. Ltd. San Bruno, Calif.).

FIGS. 5A and 5B show the amino acid sequence alignments between APOP-2 (1352286; SEQ ID NO:3) and a human LRR protein, p37NB (GI 1236329; SEQ ID NO:8), produced using the multisequence alignment program of DNASTAR™ software (DNASTAR Inc, Madison Wis.).

FIGS. 7A, 7B, 7C, 7D, 7E, 7F, and 7G show the amino acid sequence (SEQ ID NO:5) and nucleic acid sequence (SEQ ID NO:6) of APOP-3. The alignment was produced using MacDNASIS PRO™ software (Hitachi Software Engineering Co. Ltd. San Bruno, Calif.).

FIGS. 8A and 8B show the amino acid sequence alignments between APOP-3 (815087; SEQ ID NO:5) and a mouse apoptosis inducible protein, MA-3 (GI 1384078; SEQ ID NO:9), produced using the multisequence alignment program of DNASTAR™ software (DNASTAR Inc, Madison Wis.).

DESCRIPTION OF THE INVENTION

Figure 3A:
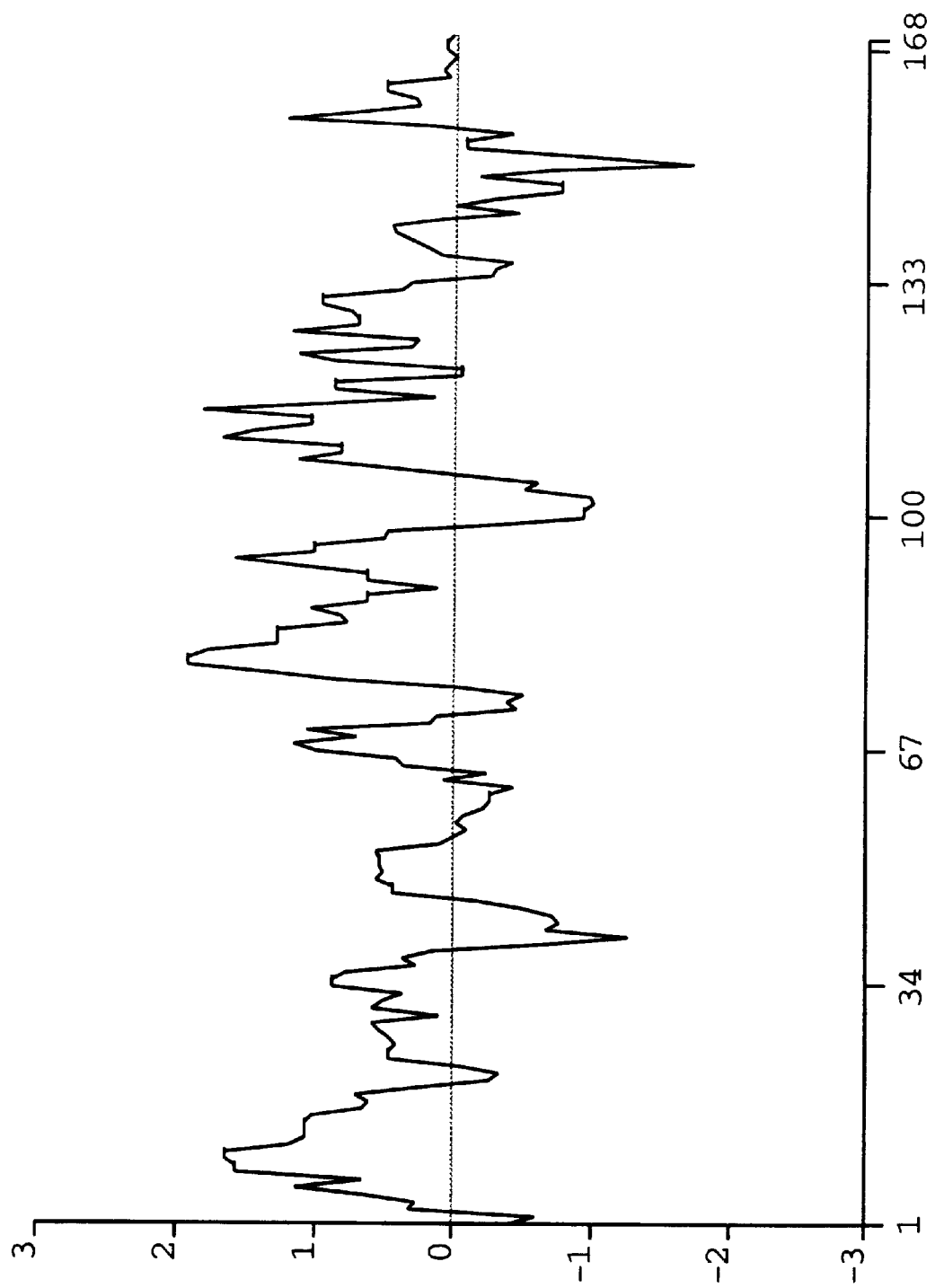
FIGS. 3A and 3B show the hydrophobicity plots for APOP-1 (SEQ ID NO:1) and the human Bcl-2 binding component 6 (SEQ ID NO:7), respectively. The positive X axis reflects amino acid position, and the negative Y axis, hydrophobicity (MacDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

APOP, as used herein, refers to the amino acid sequences of substantially purified APOP obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to APOP, increases or prolongs the duration of the effect of APOP. Agonists may include proteins, nucleic acids, carbohydrates, or any other molecules which bind to and modulate the effect of APOP.

An "allele" or "allelic sequence", as used herein, is an alternative form of the gene encoding APOP. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding APOP, as used herein, include those with deletions, insertions, or substitutions of different nucleotides resulting in a polynucleotide that encodes the same or a functionally equivalent APOP. Included within this definition are polymorphisms which may or may not be readily detectable using a particular oligonucleotide probe of the polynucleotide encoding APOP, and improper or unexpected hybridization to alleles, with a locus other than the normal chromosomal locus for the polynucleotide sequence encoding APOP. The encoded protein may also be "altered" and contain deletions, insertions, or substitutions of amino acid residues which produce a silent change and result in a functionally equivalent APOP. Deliberate amino acid substitutions may be made on the basis of similarity in polarity, charge, solubility, hydrophobicity, hydrophilicity, and/or the amphipathic nature of the residues as long as the biological or immunological activity of APOP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of APOP are preferably about 5 to about 15 amino acids in length and retain the biological activity or the immunological activity of APOP. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist", as used herein, refers to a molecule which, when bound to APOP, decreases the amount or the duration of the effect of the biological or immunological activity of APOP. Antagonists may include proteins, nucleic acids, carbohydrates, antibodies or any other molecules which decrease the effect of APOP.

As used herein, the term "antibody" refers to intact molecules as well as fragments thereof, such as Fa, F(ab')$_2$, and Fv, which are capable of binding the epitopic determinant. Antibodies that bind APOP polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic APOP, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. The composition may comprise a dry formulation or an aqueous solution. Compositions comprising polynucleotide sequences encoding APOP (SEQ ID NO:1, SEQ ID NO:3, or SEQ ID NO:5) or fragments thereof (e.g., SEQ ID NO:2, SEQ ID NO:4, SEQ ID NO:6 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding APOP in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to APOP or the encoded APOP. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides arranged on a substrate, such as paper, nylon or other type of membrane, filter, chip, glass slide, or any other suitable solid support.

The term "modulate", as used herein, refers to a change in the activity of APOP. For example, modulation may cause an increase or a decrease in protein activity, binding characteristics, or any other biological, functional or immunological properties of APOP.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, for example, a protein "comprising at least a portion of the amino acid sequence of SEQ ID NO:1" encompasses the full-length APOP-1 and fragments thereof.

The term "sample", as used herein, is used in its broadest sense. A biological sample suspected of containing nucleic acid encoding APOP, or fragments thereof, or APOP itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5X SSPE, 0.3% SDS, and 200 $\mu$ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of APOP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of three new human proteins associated with cell proliferation (hereinafter collectively referred to as "APOP"), the polynucleotides encoding APOP, and the use of these compositions for the diagnosis, prevention, or treatment of disorders associated with abnormal cell proliferation and apoptosis.

Nucleic acids encoding the APOP-1 of the present invention were first identified in Incyte Clone 358673 from a synovial cDNA library (SYNORAB01) using a computer search for amino acid sequence alignments. A consensus sequence, SEQ ID NO:2, was derived from the following overlapping and/or extended nucleic acid sequences: Incyte Clones 358673 (SYNORAB01) and 1663788 (BRSTNOT09).

Figure 3B:
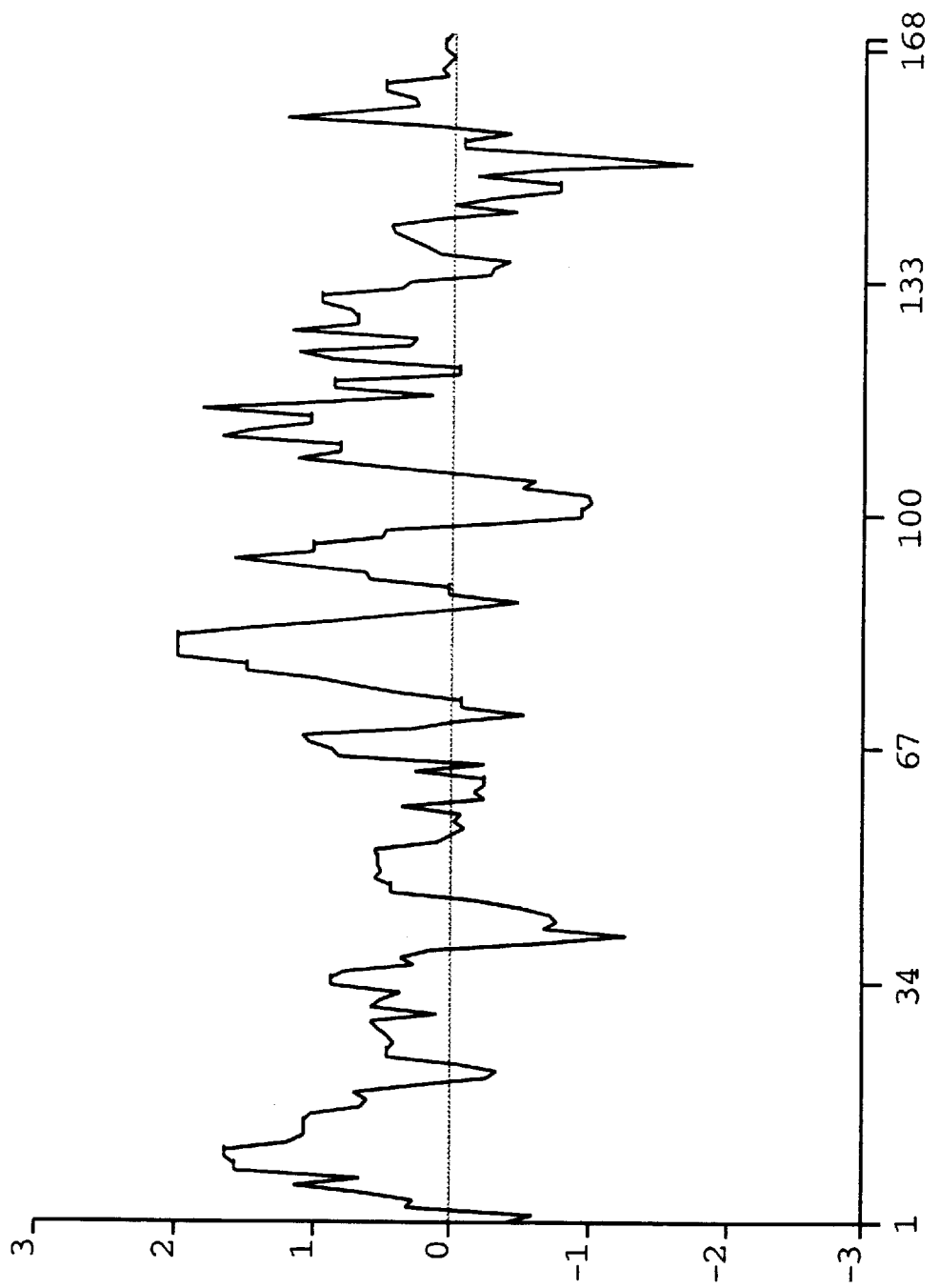

In one embodiment, the invention encompasses a polypeptide, APOP-1, comprising the amino acid sequence of SEQ ID NO:1, as shown in FIGS. 1A, 1B, and 1C. APOP-1 is 168 amino acids in length. APOP-1 has one potential cAMP- and cGMP-dependent protein kinase phosphorylation site encompassing residues R115-S118; four potential casein kinase II phosphorylation sites encompassing residues S10-E13, S16-E19, T80-D83, and S153-D156; and two potential protein kinase C phosphorylation sites encompassing residues S34-K36 and S124-K126. As shown in FIGS. 2A and 2B, APOP-11 has chemical and structural homology with a human Bcl-2 binding component 6 (GI 1683637; SEQ ID NO:7). In particular, APOP-1 and Bcl-2 binding component 6 share 85% sequence homology. As illustrated by FIGS. 3A and 3B, APOP-1 and Bcl-2 binding component 6 have rather similar hydrophobicity plots. Northern analysis shows the expression of APOP-1 in various cDNA libraries, at least 68% of which are immortalized or cancerous, at least 17% of which involve immune response, and at least 12% of which are expressed in fetal/infant tissues or organs.

Nucleic acids encoding the APOP-2 of the present invention were first identified in Incyte Clone 1352286 from a myoma tissue cDNA library (LATRTUT02) using a computer search for amino acid sequence alignments. A consensus sequence, SEQ ID NO:4, was derived from the following overlapping and/or extended nucleic acid sequences: Incyte Clones 1901255 (BLADTUT06), 3279966 and 3281759 (STOMFET02), 3141791 (SMCCNOT02), 3133726 (SMCCNOT01), 1349544, 1407110 and 1352286 (LATRTUT02), and 1357338 (LUNGNOT09).

Figure 6A:
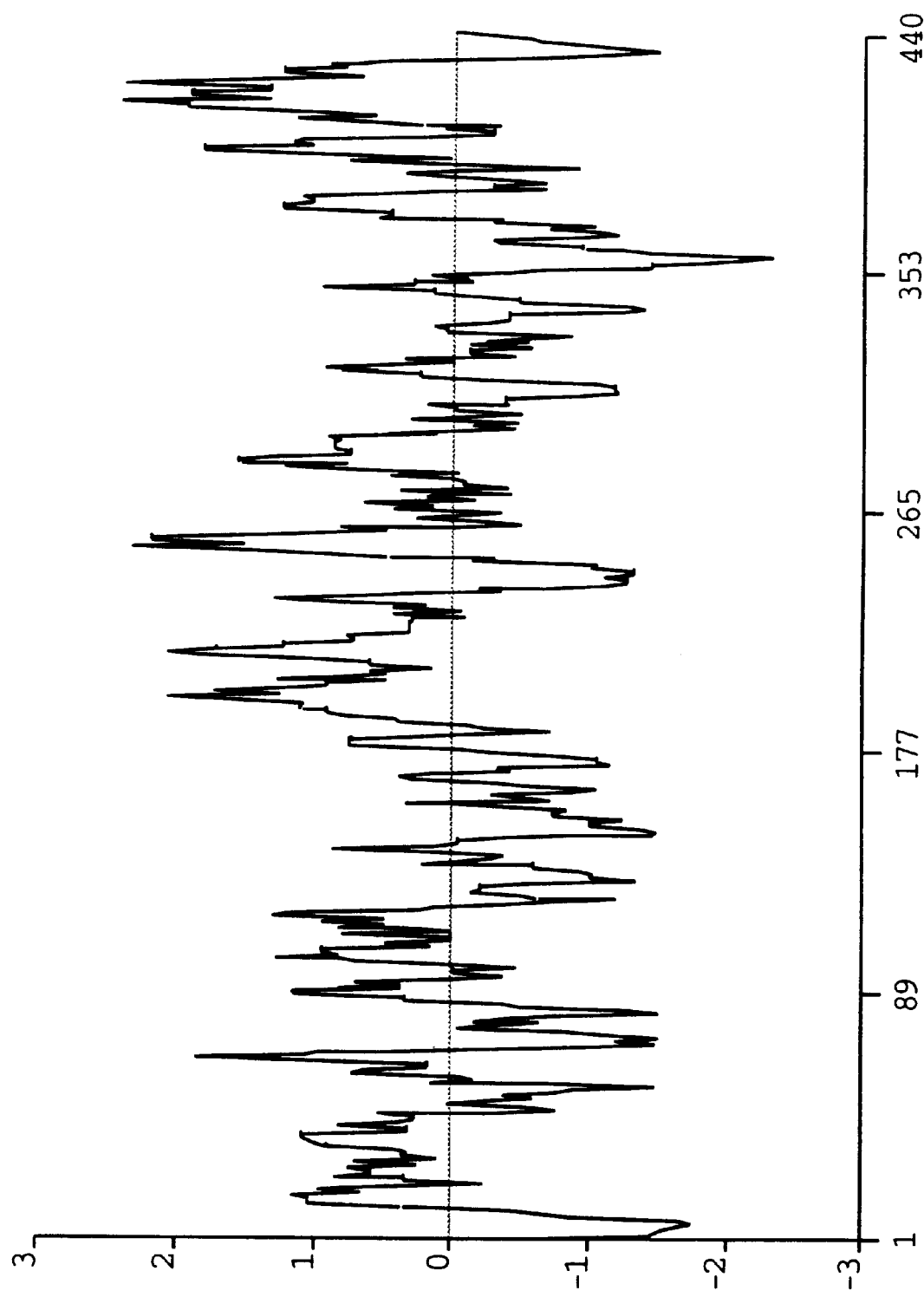
FIGS. 6A and 6B show the hydrophobicity plots for APOP-2 (SEQ ID NO:3) and p37NB (SEQ ID NO:8), respectively. The positive X axis reflects amino acid position, and the negative Y axis, hydrophobicity (MacDNASIS PRO software).
Figure 6B:
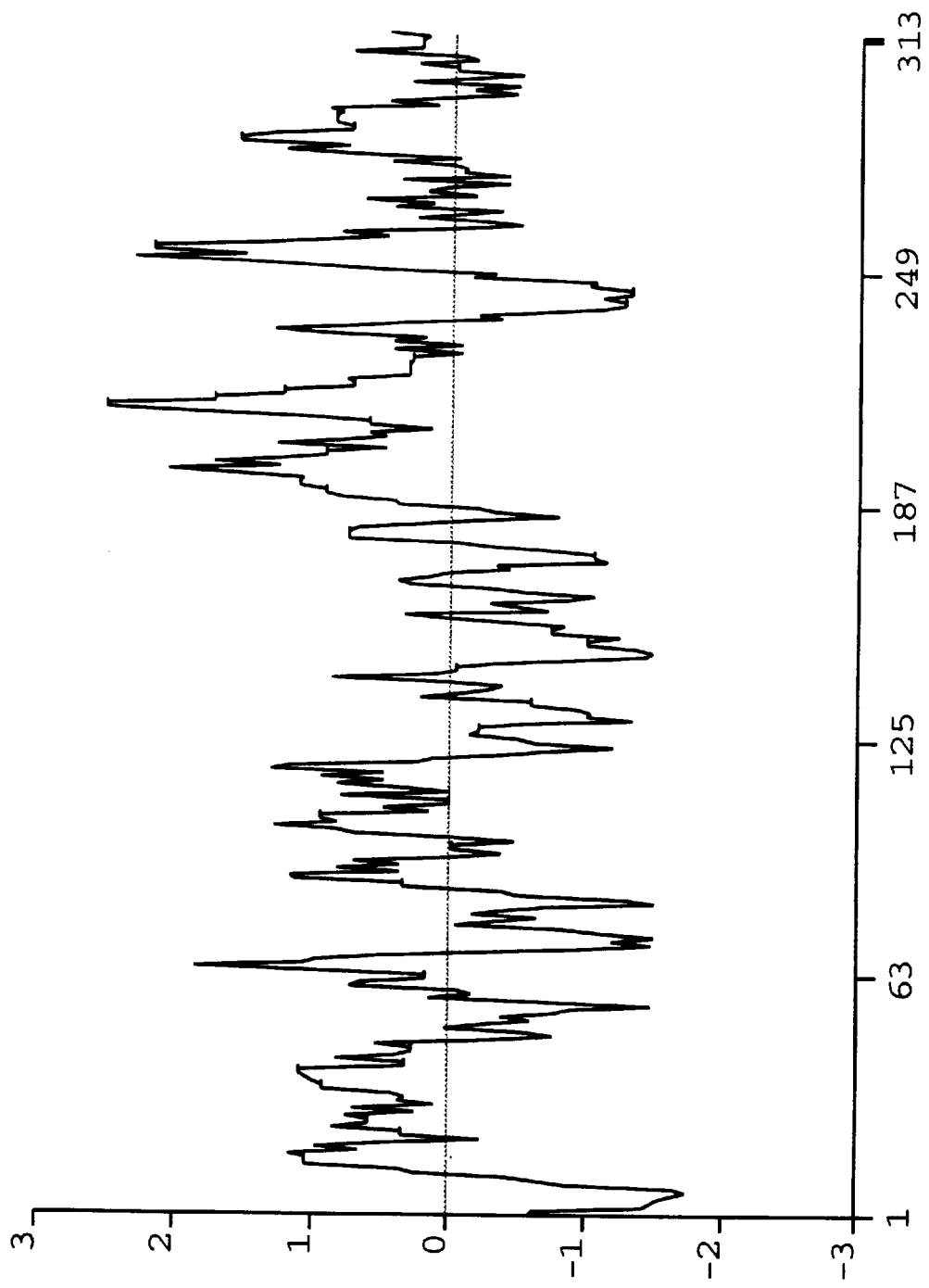

In one embodiment, the invention encompasses a polypeptide, APOP-2, comprising the amino acid sequence of SEQ ID NO:3, as shown in FIGS. 4A, 4B, and 4C. APOP-2 is 440 amino acids in length. Similar to p37NB (GI 1236329, SEQ ID NO:8), a putative LRR protein, APOP-2 has several LRR motifs which are potentially involved in protein-protein interaction. APOP-2 also has one potential amidation site encompassing residues G37-R40, two potential N-glycosylation sites encompassing residues N297-S300 and N324-L327; three potential cAMP- and cGMP-dependent protein kinase phosphorylation sites encompassing residues R19-S22, R39-S42, and K430-S433; six potential casein kinase II phosphorylation sites encompassing residues S118-E121, S194-E197, T315-E318, T379-E382, S394-E397, and T415-D418; and four potential protein kinase C phosphorylation sites encompassing residues S25-R27, T95-K97, S226-R228, and T428-K430. As shown in FIGS. 5A and 5B, APOP-2 has chemical and structural homology with a human LRR protein, p37NB (GI 1236329; SEQ ID NO:8). In particular, APOP-2 and p37NB share 74% sequence homology. As illustrated by FIGS. 6A and 6B, APOP-2 and p37NB have rather similar hydrophobicity plots. Northern analysis shows the expression of APOP-2 in various cDNA libraries, at least 27% of which are immortalized or cancerous, at least 15% of which involve immune response, and at least 50% of which are expressed in fetal/infant tissues or organs.

Nucleic acids encoding the APOP-3 of the present invention were first identified in Incyte Clone 815087 from an ovarian tumor tissue cDNA library (OVARTUT01) using a computer search for amino acid sequence alignments. A consensus sequence, SEQ ID NO:6, was derived from the following overlapping and/or extended nucleic acid sequences: Incyte Clones 1697887 (BLADTUT05), 140813 (TLYMNOR01), 1291763 (PGANNOT03), 2741788 (BRSTTUT14), 2236154 (PANCTUT02), 1610527 (COLNTUT06), 2518507 (BRAITUT21), 815087 (OVARTUT01), and sequence SAEA00394.

Figure 9A:
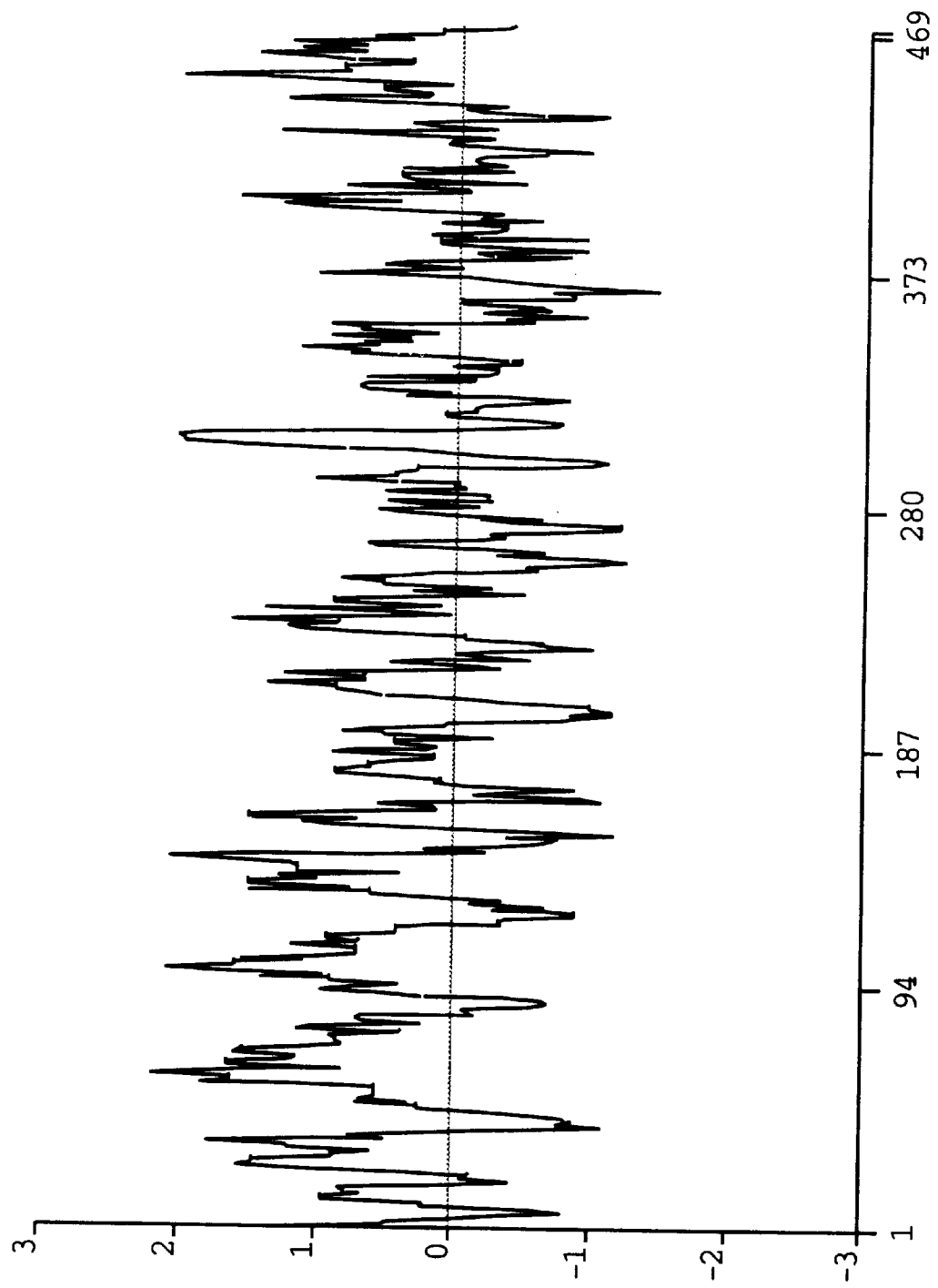
FIGS. 9A and 9B show the hydrophobicity plots for APOP-3 (SEQ ID NO:5) and MA-3 (SEQ ID NO:9), respectively. The positive X axis reflects amino acid position, and the negative Y axis, hydrophobicity (MacDNASIS PRO software).
Figure 9B:
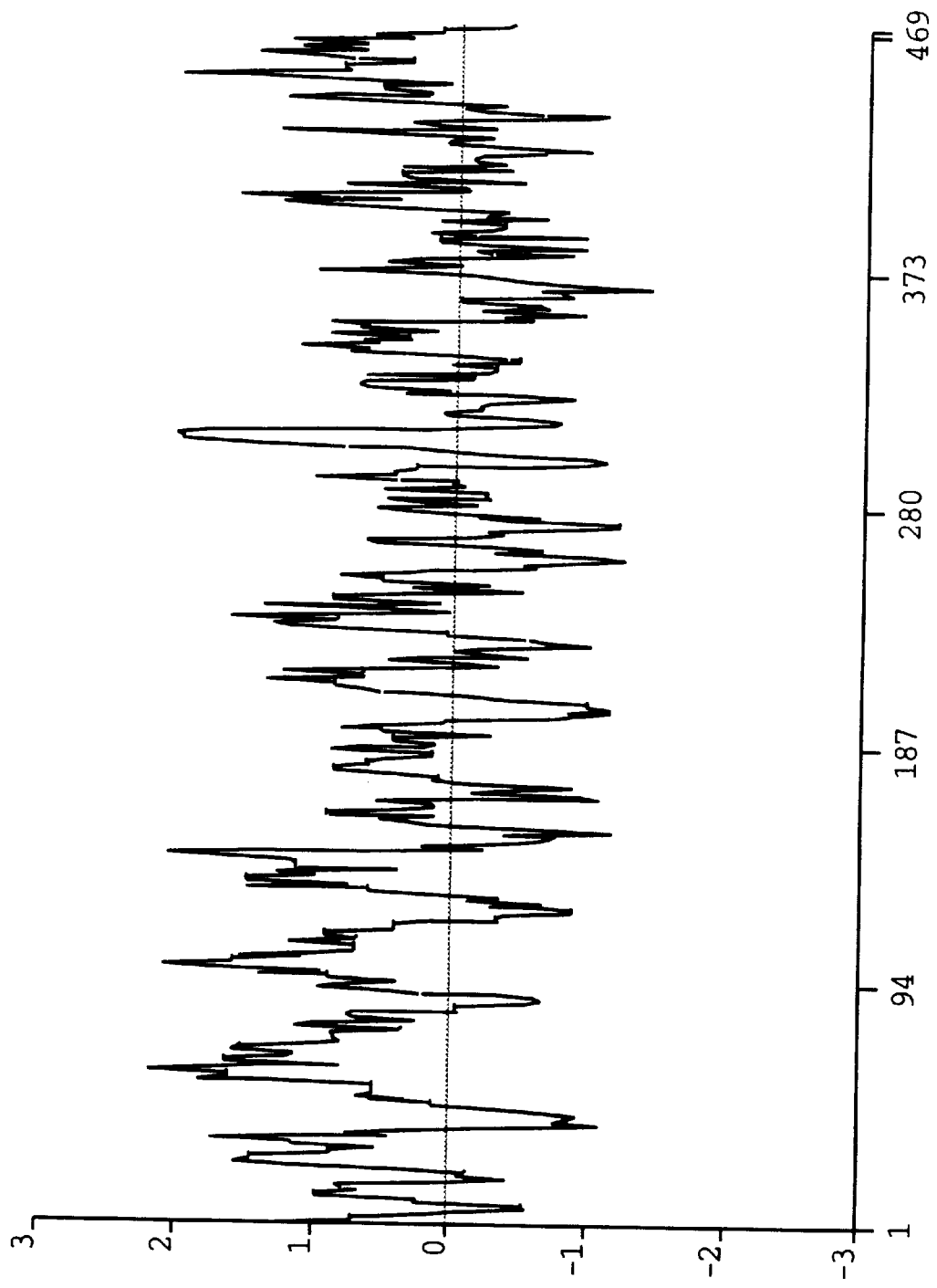

In one embodiment, the invention encompasses a polypeptide, APOP-3, comprising the amino acid sequence of SEQ ID NO:5, as shown in FIGS. 7A, 7B, 7C, 7D, 7E, 7F, and 7G. APOP-3 is 469 amino acids in length. APOP-3 has two potential N-glycosylation sites encompassing residues N18-D21 and N66-R69; two potential cAMP- and cGMP-dependent protein kinase phosphorylation sites encompassing residues R64-S67 and R310-S313; 13 potential casein kinase II phosphorylation sites encompassing residues S25-E28, S49-E52, S67-D70, S76-D79, S80-D83, S214-E217, S232-D235, T234-E237, T277-D280, S345-E348, S374-E377, S424-E427, and S457-D460; nine potential protein kinase C phosphorylation sites encompassing residues S67-R69, S71-R73, S94-K96, S 106-K108, S214-R216, T219-K221, T254-R256, S281 -K283, and T379-K381; one potential cell attachment sequence encompassing residues R73-D75; and one potential tyrosine kinase phosphorylation site encompassing residues K402-Y409. As shown in FIG. 8, APOP-3 has chemical and structural homology with a mouse apoptosis-associated protein, MA-3 (GI 1384078; SEQ ID NO:9). In particular, APOP-3 and MA-3 share 96% sequence homology. As illustrated by FIGS. 9A and 9B, APOP-3 and MA-3 have rather similar hydrophobicity plots. Northern analysis shows the expression of APOP-3 in various cDNA libraries, at least 48% of which are immortalized or cancerous, and at least 30% of which involve immune response, and at least 8% of which are expressed in fetal/infant tissues or organs.

The invention also encompasses APOP variants. A preferred APOP variant is one which has at least about 80%, more preferably at least about 90%, and most preferably at least about 95% amino acid sequence identity to the APOP amino acid sequence, and which contains at least onebiological, immunological or other functional characteristic or activity of APOP. A most preferred APOP variant is one having at least 95% amino acid sequence which encodes APOP.

The invention also encompasses polynucleotides which encode APOP. Accordingly, any nucleic acid sequence which encodes the amino acid sequence of APOP can be used to produce recombinant molecules which express APOP. In a particular embodiment, the invention encompasses a polynucleotide sequence comprising the sequence of SEQ ID NO:2, as shown, in FIGS. 1A, 1B, and 1C, which encodes an APOP. In a further embodiment, the invention encompasses a polynucleotide sequence comprising the sequence of SEQ ID NO:4, as shown in FIGS. 4A, 4B, 4C, 4D, and 4F, which encodes an APOP. Still further, the invention encompasses a polynucleotide sequence comprising the sequence of SEQ ID NO:6, as shown in FIGS. 7A, 7B, 7C, 7D, 7E, 7F and 7G, which encodes an APOP.

The invention also encompasses a variant of a polynucleotide sequence encoding APOP. In particular, such a variant polynucleotide sequence will have at least about 80%, more preferably at least about 90%, and most preferably at least about 95% polynucleotide sequence identity to the polynucleotide sequence encoding APOP. A particular aspect of the invention encompasses a variant of SEQ ID NO:2, which has at least about 80%, more preferably at least about 90%, and most preferably at least about 95% polynucleotide sequence identity to SEQ ID NO:2. The invention further encompasses a polynucleotide variant of SEQ ID NO:4 having at least about 80%, more preferably at least about 90%, and most preferably at least about 95% polynucleotide sequence identity to SEQ ID NO:4. Still further, the invention encompasses a polynucleotide variant of SEQ ID NO:6 having at least about 80%, more preferably at least about 90%, and most preferably at least about 95% polynucleotide sequence identity to SEQ ID NO:6. Any one of the polynucleotide variants described above can encode an amino acid sequence which contains at least one biological, immunological or other functional characteristic or activity of APOP.

It will be appreciated by those skilled in the art that as a result of the degeneracy of the genetic code, a multitude of nucleotide sequences encoding APOP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring APOP, and all such variations are to be considered as being specifically disclosed.

Although nucleotide sequences which encode APOP and its variants are preferably capable of hybridizing to the nucleotide sequence of the naturally occurring APOP under appropriately selected conditions of stringency, it may be advantageous to produce nucleotide sequences encoding APOP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding APOP and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode APOP and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding APOP or any fragment thereof.

Also encompassed by the invention are polynucleotide sequences that are capable of hybridizing to the claimed nucleotide sequences, and, in particular, those shown in SEQ ID NO:2, SEQ ID NO:4, or SEQ ID NO:6, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by GIBCO/BRL (Gaithersburg, Md.). Preferably, the process is automated with machines such as the Hamilton Micro Lab 2200 (Hamilton, Reno, Neva.), Peltier Thermal Cycler (PTC200; MJ Research, Watertown, Mass.) and the ABI Catalyst and 373 and 377 DNA Sequencers (Perkin Elmer).

The nucleic acid sequences encoding APOP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode APOP may be used in recombinant DNA molecules to direct expression of APOP, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express APOP.

As will be understood by those of skill in the art, it may be advantageous to produce APOP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter APOP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding APOP may be ligated to a heterologous sequence to encode a fusion protein. For example, to screen peptide libraries for inhibitors of APOP activity, it may be useful to encode a chimeric APOP protein that can be recognized by a commercially available antibody. A fusion protein may also be engineered to contain a cleavage site located between the APOP encoding sequence and the heterologous protein sequence, so that APOP may be cleaved and purified away from the heterologous moiety.

In another embodiment, sequences encoding APOP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of APOP, or a fragment thereof. For example, peptide synthesis can be performed using various solid-phase techniques (Roberge, J. Y. et al. (1995) Science 269:202–204) and automated synthesis may be achieved, for example, using the ABI431A Peptide Synthesizer (Perkin Elmer).

The newly synthesized peptide may be substantially purified by preparative high performance liquid chromatography (e.g., Creighton, T. (1983) Proteins, Structures and Molecular Principles, W H Freeman and Co., New York, N.Y.). The composition of the synthetic peptides may be confirmed by amino acid analysis or sequencing (e.g., the Edman degradation procedure; Creighton, supra). Additionally, the amino acid sequence of APOP, or any part thereof, may be altered during direct synthesis and/or combined using chemical methods with sequences from other proteins, or any part thereof, to produce a variant polypeptide.

In order to express a biologically active APOP, the nucleotide sequences encoding APOP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding APOP and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding APOP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding APOP, vectors based on SV40 or EBV may be used with an appropriate selectable marker.

In bacterial systems, a number of expression vectors may be selected depending upon the use intended for APOP. For example, when large quantities of APOP are needed for the induction of antibodies, vectors which direct high level expression of fusion proteins that are readily purified may be used. Such vectors include, but are not limited to, the multifunctional E. coli cloning and expression vectors such as Bluescript® (Stratagene), in which the sequence encoding APOP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wiss.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding APOP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express APOP. For example, in one such system, *Autographa californica* nuclear polyhedrosis virus (AcNPV) is used as a vector to express foreign genes in *Spodoptera frugiperda* cells or in *Trichoplusia* larvae. The sequences encoding APOP may be cloned into a non-essential region of the virus, such as the polyhedrin gene, and placed under control of the polyhedrin promoter. Successful insertion of APOP will render the polyhedrin gene inactive and produce recombinant virus lacking coat protein. The recombinant viruses may then be used to infect, for example, *S. frugiperda* cells or *Trichoplusia* larvae in which APOP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding APOP may be ligated into an adenovirus transcription/translation complex consisting of the late promoter and tripartite leader sequence. Insertion in a non-essential E1 or E3 region of the viral genome may be used to obtain a viable virus which is capable of expressing APOP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding APOP. Such signals include the ATG initiation codon and adjacent sequences. In cases where sequences encoding APOP, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express APOP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻or aprt⁻cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding APOP is inserted within a marker gene sequence, transformed cells containing sequences encoding APOP can be identified by the absence of marker gene function. Alternatively, a marker gene can be placed in tandem with a sequence encoding APOP under the control of a single promoter. Expression of the marker gene in response to induction or selection usually indicates expression of the tandem gene as well.

Alternatively, host cells which contain the nucleic acid sequence encoding APOP and express APOP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding APOP can be detected by DNA-DNA or DNA-RNA hybridization or amplification using probes or fragments or fragments of polynucleotides encoding APOP. Nucleic acid amplification based assays involve the use of oligonucleotides or oligomers based on the sequences encoding APOP to detect transformants containing DNA or RNA encoding APOP.

A variety of protocols for detecting and measuring the expression of APOP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on APOP is preferred, but a competitive binding assay may be employed. These and other assays are described, among other places, in Hampton, R. et al. (1990; *Serological Methods, a Laboratory Manual*, APS Press, St Paul, Minn.) and Maddox, Del. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding APOP include oligolabeling, nick translation, end-labeling or PCR amplification using a labeled nucleotide. Alternatively, the sequences encoding APOP, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding APOP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode APOP may be designed to contain signal sequences which direct secretion of APOP through a prokaryotic or eukaryotic cell membrane. Other constructions may be used to join sequences encoding APOP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and APOP may be used to facilitate purification. One such expression vector provides for expression of a fusion protein containing APOP and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying APOP from the fusion protein. A discussion of vectors which contain fusion proteins is provided in Kroll, D. J. et al. (1993; DNA Cell Biol. 12:441–453).

In addition to recombinant production, fragments of APOP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of APOP may be chemically synthesized separately and combined using chemical methods to produce the full length molecule.

Therapeutics

Chemical and structural homology exists between APOP-1 and a human Bcl-2 binding component 6 (GI 1683637; SEQ ID NO:7); between APOP-2 and a human LRR protein, p37NB (GI 1236329; SEQ ID NO:8); and between APOP-3 and a mouse apoptosis inducible protein, MA-3 (GI 1384078; SEQ ID NO:9). Northern analysis of APOP (SEQ ID NO:1, SEQ ID NO:3, or SEQ ID NO:5) expression suggests a close association with cell proliferation, inflammation, and fetal/infant development. Therapeutic uses for all three polypeptides are described collectively below.

In cancers where APOP inhibits cell prolferation, it is desirable to increase the expression of APOP. Therefore, in one embodiment, APOP, or a fragment or a derivative thereof, may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a pharmaceutical composition comprising APOP may be administered to a subject to prevent or treat a cancer including, but not limited to, those listed above.

In still another embodiment, an agonist which is specific for APOP may be administered to prevent or treat a cancer including, but not limited to, those listed above.

In a further embodiment, a vector capable of expressing APOP, or a fragment or a derivative thereof, may be used to prevent or treat a cancer including, but not limited to, those listed above.

In disorders associated with an increase in apoptosis where APOP inhibits apoptosis, it is desirable to increase the expression of APOP. Therefore, in one embodiment, APOP or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising APOP may be administered to a subject to prevent or treat a disorder associated with increased apoptosis including, but not limited to, those listed above.

In still another embodiment, an agonist which is specific for APOP may be administered to prevent or treat a disorder associated with increased apoptosis including, but not limited to, those listed above.

In a further embodiment, a vector capable of expressing APOP, or a fragment or a derivative thereof, may be used to prevent or treat a disorder associated with increased apoptosis including, but not limited to, those listed above.

In cancers where APOP promotes cell proliferation, it is desirable to decrease its activity. Therefore, in one embodiment, an antagonist of APOP, or a fragment or a derivative thereof, may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for APOP may be used directly as an antagonist, or indirectly as a targeting or delivery mechanism for bringing a pharmaceutical agent to cells or tissue which express APOP.

In another embodiment, a vector expressing the complement of the polynucleotide encoding APOP, or a fragment or a derivative thereof, may be administered to a subject to prevent or treat a disorder associated with cell proliferation including, but not limited to, the types of cancer listed above.

In inflammation where APOP promotes cell proliferation, it is desirable to decrease its activity. Therefore, in one embodiment, an antagonist of APOP, or a fragment or a derivative thereof, may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for APOP may be used directly as an antagonist, or indirectly as a targeting or delivery mechanism for bringing a pharmaceutical agent to cells or tissue which express APOP.

In another embodiment, a vector expressing the complement of the polynucleotide encoding APOP, or a fragment or a derivative thereof, may be administered to a subject to prevent or treat an inflammation associated with any disorder including, but not limited to, those listed above.

In disorders associated with an increase in apoptosis where APOP stimulates apoptosis, it is desirable to decrease its activity. Therefore, in one enbodiment, an antagonist of APOP or a fragment or derivative thereof may be added to cells to stimulate cell proliferation. In particular, APOP may be added to a cell or cells in vivo using delivery mechanisms such as liposomes, viral based vectors, or electroinjection for the purpose of promoting regeneration or cell differentiation of the cell or cells. In addition, APOP may be added to a cell, cell line, tissue or organ culture in vitro or ex vivo to stimulate cell proliferation for use in heterologous or autologous transplantation. In some cases, the cell will have been selected for its ability to fight an infection or a cancer or to correct a genetic defect in a disease such as sickle cell anemia, β thalassemia, cystic fibrosis, or Huntington's chorea. In one aspect, an antibody specific for APOP may be used directly as an antagonist, or indirectly as a targeting or delivery mechanism for bringing a pharmaceutical agent to cells or tissue which express APOP.

In another further embodiment, a vector expressing the complement of the polynucleotide encoding APOP, or a fragment or a derivative thereof, may be may be added to cells to stimulate cell proliferation, as described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of APOP may be produced using methods which are generally known in the art. In particular, purified APOP may be used to produce antibodies or to screen libraries of pharmaceutical agents to identify those which specifically bind APOP.

Antibodies to APOP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with APOP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and Corynebacterium parvum are especially preferable.

It is preferred that the oligopeptides, peptides, or fragments used to induce antibodies to APOP have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of APOP amino acids may be fused with those of another protein such as keyhole limpet hemocyanin and antibody produced against the chimeric molecule.

Monoclonal antibodies to APOP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce APOP-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for APOP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between APOP and its specific antibody. A two-site, monoclonal-based immunoassay utilizing monoclonal antibodies reactive to two non-interfering APOP epitopes is preferred, but a competitive binding assay may also be employed (Maddox, supra).

In another embodiment of the invention, the polynucleotides encoding APOP, or any fragment or complement thereof, may be used for therapeutic purposes. In one aspect, the complement of the polynucleotide encoding APOP may be used in situations in which it would be desirable to block the transcription of the mRNA. In particular, cells may be transformed with sequences complementary to polynucleotides encoding APOP. Thus, complementary molecules or fragments may be used to modulate APOP activity, or to achieve regulation of gene function. Such technology is now well known in the art, and sense or antisense oligonucleotides or larger fragments, can be designed from various locations along the coding or control regions of sequences encoding APOP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding APOP. These techniques are described both in Sambrook et al. (supra) and in Ausubel et al. (supra).

Genes encoding APOP can be turned off by transforming a cell or tissue with expression vectors which express high levels of a polynucleotide or fragment thereof which encodes APOP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding APOP (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding APOP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding APOP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of APOP, antibodies to APOP, mimetics, agonists, antagonists, or inhibitors of APOP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of APOP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example APOP or fragments thereof, antibodies of APOP, agonists, antagonists or inhibitors of APOP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind APOP may be used for the diagnosis of conditions or diseases characterized by expression of APOP, or in assays to monitor patients being treated with APOP, agonists, antagonists or inhibitors. The antibodies useful for diagnostic purposes may be prepared in the same manner as those described above for therapeutics. Diagnostic assays for APOP include methods which utilize the antibody and a label to detect APOP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring APOP are known in the art and provide a basis for diagnosing altered or abnormal levels of APOP expression. Normal or standard values for APOP expression are established by combining body fluids or cell extracts taken from normal mammalian subjects, preferably human, with antibody to APOP under conditions suitable for complex formation. The amount of standard complex formation may be quantified by various methods, but preferably by photometric means. Quantities of APOP expressed in subject, samples, control and disease, from biopsied tissues are compared with the standard values. Deviation between standard and subject values establishes the parameters for diagnosing disease.

In another embodiment of the invention, the polynucleotides encoding APOP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of APOP may be correlated with disease. The diagnostic assay may be used to distinguish between absence, presence, and excess expression of APOP, and to monitor regulation of APOP levels during therapeutic intervention.

In one aspect, hybridization with PCR probes which are capable of detecting polynucleotide sequences, including genomic sequences, encoding APOP or closely related molecules, may be used to identify nucleic acid sequences which encode APOP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding APOP, alleles, or related sequences.

Probes may also be used for the detection of related sequences, and should preferably contain at least 50% of the nucleotides from any of the APOP encoding sequences. The hybridization probes of the subject invention may be DNA or RNA and derived from the nucleotide sequence of SEQ ID NO:2, SEQ ID NO:4, SEQ ID NO:6, or from genomic sequence including promoter, enhancer elements, and introns of the naturally occurring APOP.

Means for producing specific hybridization probes for DNAs encoding APOP include the cloning of nucleic acid sequences encoding APOP or APOP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding APOP may be used for the diagnosis of conditions or disorders which are associated with expression of APOP. Examples of such conditions or disorders include, but are not limited to, cancers such as adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders with associated inflammation such as Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation,osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; disorders with associated apoptosis such as AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis. The polynucleotide sequences encoding APOP may be used in Southern or northern analysis, dot blot, or other membrane-based technologies; in PCR technologies; or in dipstick, pin, ELISA assays or microarrays utilizing fluids or tissues from patient biopsies to detect altered APOP expression. Such qualitative or quantitative methods are well known in the art.

In a particular aspect, the nucleotide sequences encoding APOP may be useful in assays that detect activation or induction of various cancers, particularly those mentioned above. The nucleotide sequences encoding APOP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding APOP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of APOP, a normal or standard profile for expression is established. This may be accomplished by combining body fluids or cell extracts taken from normal subjects, either animal or human, with a sequence, or a fragment thereof, which encodes APOP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding APOP may involve the use of PCR. Such oligomers may be chemically synthesized, generated enzymatically, or produced in vitro. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of APOP include radiolabeling or biotinylating nucleotides, coamplification of a control nucleic acid, and standard curves onto which the experimental results are interpolated (Melby, P. C. et al. (1993) J. Immunol. Meth., 159:235–244; Duplaa, C. et al. (1993) Anal. Biochem. 211:229–236). The speed of quantitation of multiple samples may be accelerated by running the assay in an ELISA format where the oligomer of interest is presented in various dilutions and a spectrophotometric or calorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations, and polymorphisms. This information will be useful in determining gene function, understanding the genetic basis of disease, diagnosing disease, and in developing and monitoring the activity of therapeutic agents In one embodiment, the microarray is prepared and used according to the methods known in the art such as those described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619).

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably about 15 to 30 nucleotides in length, and most preferably about 20 to 25 nucleotides in length. For a certain type of microarray, it may be preferable to use oligonucleotides which are only 7 to 10 nucleotides in length. The microarray may contain oligonucleotides which cover the known 5' (or 3') sequence, or may contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from 2 to 1,000,000.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon or any other type of membrane, filter, chip, glass slide, or any other suitable solid support.

In one aspect, the oligonucleotides may be synthesized on the surface of the substrate by using a chemical coupling procedure and an ink jet application apparatus, such as that described in PCT application WO95/251116 (Baldeschweiler et al.). In another aspect, a "gridded" array analogous to a dot or slot blot (HYBRIDOT® apparatus, GIBCO/BRL) may be used to arrange and link cDNA fragments or oligonucleotides to the surface of a substrate using a vacuum system, thermal, UV, mechanical or chemical bonding procedures. In yet another aspect, an array may be produced by hand or by using available devices, materials, and machines (including Brinkmann® multichannel pipettors or robotic instruments) and may contain 8, 24, 96, 384, 1536 or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and Oligolabeling or TransProbe kits (Pharmacia) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. A detection system may be used to measure the absence, presence, and amount of hybridization for all of the distinct sequences simultaneously. This data may be used for large scale correlation studies or functional analysis of the sequences, mutations, variants, or polymorphisms among samples (Heller, R. A. et al., (1997) Proc. Natl. Acad. Sci. 94:2150–55).

In another embodiment of the invention, the nucleic acid sequences which encode APOP may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding APOP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, APOP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between APOP and the agent being tested, may be measured.

Another technique for drug screening which may be used provides for high throughput screening of compounds having suitable binding affinity to the protein of interest as described in published PCT application WO84/03564. In this method, as applied to APOP large numbers of different small test compounds are synthesized on a solid substrate, such as plastic pins or some other surface. The test compounds are reacted with APOP, or fragments thereof, and washed. Bound APOP is then detected by methods well known in the art. Purified APOP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding APOP specifically compete with a test compound for binding APOP. In this manner, the antibodies can be used to detect the presence of any peptide which shares one or more antigenic determinants with APOP.

In additional embodiments, the nucleotide sequences which encode APOP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

The SYNORAB01 cDNA library was constructed from RNA isolated from hip synovial tissue removed from a 68 year old Caucasian with rheumatoid arthritis during hip replacement surgery. The frozen tissue was ground in a mortar and pestle and lysed immediately in a buffer containing guanidinium isothiocyanate. The lysate was extracted with acid phenol and centrifuged over a 5.7 M CsCl cushion using a Beckman SW28 rotor in a Beckman L8-70M Ultracentrifuge (Beckman Instruments) for 18 hours at 25,000 rpm at ambient temperature. The RNA was precipitated using 0.3 M sodium acetate and 2.5 volumes of ethanol, resuspended in water and DNase treated for 15 min at 37° C. The RNA was isolated using the Qiagen Oligotex kit (QIAGEN, Chatsworth, Calif.) and used to construct the cDNA library.

cDNA synthesis was primed using a combination of oligo d(T) and random primers, and synthetic adaptor oligonucleotides were ligated onto the cDNA ends to enable insertion into the Uni-ZAP™ vector system (Stratagene). E. coli host strain XL1-Blue® (Stratagene) was co-transfected with phagemid and f1 helper phage particles. Proteins derived from both the lambda phage and f1 helper phage initiated new DNA synthesis from defined sequences on the lambda target DNA to create the smaller, single-stranded circular pBluescript® phagemid (Stratagene) which contains the SYNORAB01 inserts. When the phagemid DNA was released from the cells, it was purified and used to reinfect fresh bacterial host cells (SOLR™; Stratagene). Transformed bacteria expressing the β-lactamase gene on the phagemid survived selection on medium containing ampicillin and produced double-stranded phagemid.

The LATRTUT02 cDNA library was constructed from cancerous heart tissue removed from a 43-year-old Caucasian male who had undergone annuloplasty following diagnosis of atrial myxoma. The frozen tissue was homogenized and lysed using a Brinkmann Homogenizer Polytron PT-3000. (Brinkmann Instruments, Westbury, N..J.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the Qiagen Oligotex kit (QIAGEN) and used to construct the cDNA library.

The OVARTUT01 cDNA library was constructed from tumorous ovary tissue obtained by salpingo-oophorectomy of a 43 year old Caucasian female to remove an ovary which had been diagnosed with a malignant neoplasm. The frozen tissue was homogenized and lysed using a Brinkmann Homogenizer Polytron PT-3000 (Brinkmann Instruments) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.0, precipitated using 0.3 M sodium acetate and 2.5 volumes of ethanol, resuspended in RNAse-free water and DNase treated at 37° C. The RNA extraction and precipitation were repeated as before. The mRNA was then isolated using the Qiagen Oligotex kit (QIAGEN) and used to construct the cDNA library.

The mRNA was handled according to the recommended protocols in the SuperScript Plasmid System for cDNA Synthesis and Plasmid Cloning (Cat. #18248-013,GIBCO/BRL). The cDNAs were fractionated on a Sepharose CL4B column (Cat. #275105-01; Pharmacia), and those cDNAs exceeding 400 bp were ligated into pINCY I (LATRTUT02) or pSport 1 (OVARTUT01). The plasmids were subsequently transformed into DH5a™ competent cells (Cat. #18258-012; GIBCO/BRL).

II Isolation and Sequencing of cDNA Clones

Phagemid DNA for SYNORAB01 was purified using the QIAWELL-8 plasmid purification system (QIAGEN) and prepared for sequencing. Chain termination reaction products were electrophoresed on urea-polyacrylamide gels and detected by fluorescence.

Plasmid cDNA for LATRTUT02 or OVARTUT01 was released from the cells and purified using the REAL Prep 96 Plasmid Kit (Catalog #26173, QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs for all three libraries were sequenced according to the method of Sanger et al. (1975, J. Mol. Biol. 94:441f), using the Perkin Elmer Catalyst 800 or a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems or the Perkin Elmer 373 DNA Sequencing System and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul SF (1993) J. Mol. Evol. 36:290–300; Altschul, SF et al. (1990) J. Mol. Biol. 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith RF and TF Smith (1992 Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (1993; Proc Nat Acad Sci 90:5873–7) and incorporated herein by reference, searches matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) *J.Mol.Evol.* 36:290–300; Altschul, S. F. et al. (1990) *J.Mol.Evol,* 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\%\text{ sequence identity} \times \%\text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding APOP occurs. Abundance and percent abundance are also reported. Abundance directly reflects the number of times a particular transcript is represented in a cDNA library, and percent abundance is abundance divided by the total number of sequences examined in the cDNA library.

V Extension of APOP Encoding Polynucleotides

The nucleic acid sequence of the Incyte Clones 358673, 1352286, or 815087 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (GIBCO/BRL) were used to extend the sequence. If is more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 µl of liquid LB/12x Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2, SEQ ID NO:4, or SEQ ID NO:6 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [γ-$^{32}$p] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, one of the nucleotide sequences of the present invention are examined using a computer algorithm which starts at the 3' end of the nucleotide sequence. The algorithm identified oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This processis repeated for each gene in the microarray, and double sets of twenty 20 mers are synthesized and arranged on the surface of the silicon chip using a light-directed chemical process, such as that discussed in Chee, supra.

In the alternative, a chemical coupling procedure and an ink jet device are used to synthesize oligomers on the surface of a substrate (cf. Baldeschweiler, supra). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. A typical array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned image is examined to determine degree of complementarity and the relative abundance/expression level of each oligonucleotide sequence in the microarray.

VIII Complementary Polynucleotides

Sequence complementary to the APOP-encoding sequence, or any part thereof, is used to decrease or inhibit expression of naturally occurring APOP. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of APOP, SEQ ID NO: 1, SEQ ID NO:3, or SEQ ID NO:5. To inhibit transcription, a complementary oligonucleotide is designed from the most unique 5' sequence and used to prevent promoter binding to the coding sequence. To inhibit translation, a complementary oligonucleotide is designed to prevent ribosomal binding to the APOP-encoding transcript.

IX Expression of APOP

Expression of APOP is accomplished by subcloning the cDNAs into appropriate vectors and transforming the vectors into host cells. In this case, the cloning vector is also used to express APOP in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of APOP into the bacterial growth media which can be used directly in the following assay for activity.

X Demonstration of APOP Activity

APOP can be expressed by transforming a mammalian cell line such as COS7, HeLa or CHO with an eukaryotic expression vector encoding APOP. Eukaryotic expression vectors are commercially available, and the techniques to introduce them into cells are well known to those skilled in the art. The cells with and without the APOP expression vector are incubated for 48–72 hours after transformation under conditions appropriate for the cell line to allow expression of APOP. Phase microscopy is subsequently used to compare the mitotic index of transformed versus control cells. An increase in the mitotic index where APOP stimulates cell proliferation indicates APOP activity. Likewise, a decrease in cell numbers where APOP stimulates apoptosis indicates APOP activity.

XI Production of APOP Specific Antibodies

APOP that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring APOP Using Specific Antibodies

Naturally occurring or recombinant APOP is substantially purified by immunoaffinity chromatography using antibodies specific for APOP. An immunoaffinity column is constructed by covalently coupling APOP antibody to an activated chromatographic resin, such as CNBr-activated Sepharose (Pharmacia & Upjohn). After the coupling, the resin is blocked and washed according to the manufacturer's instructions.

Media containing APOP is passed over the immunoaffinity column, and the column is washed under conditions that allow the preferential absorbance of APOP (e.g., high ionic strength buffers in the presence of detergent). The column is eluted under conditions that disrupt antibody/APOP binding (eg, a buffer of pH 2–3 or a high concentration of a chaotrope, such as urea or thiocyanate ion), and APOP is collected.

XIII Identification of Molecules Which Interact with APOP

APOP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled APOP, washed and any wells with labeled APOP complex are assayed. Data obtained using different concentrations of APOP are used to calculate values for the number, affinity, and association of APOP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 168 amino acids
        (B) TYPE: amino acid
        (C) STRANDEDNESS: single
        (D) TOPOLOGY: linear (vii) IMMEDIATE SOURCE:
        (A) LIBRARY: SYNORAB01
        (B) CLONE: 358673

(xi) SEQUENCE DESCRIPTION: SEQ ID NO:1:

```
Met Phe Gln Ile Pro Glu Phe Glu Pro Ser Glu Gln Glu Asp Ser Ser
 1               5                  10                  15
```

```
Ser Ala Glu Arg Gly Leu Gly Pro Ser Pro Ala Gly Asp Gly Pro Ser
         20                  25                  30

Gly Ser Gly Lys His His Arg Gln Ala Pro Gly Leu Leu Trp Asp Ala
             35                  40                  45

Ser His Gln Gln Glu Gln Pro Thr Ser Ser Ser His His Gly Gly Ala
 50                  55                  60

Gly Ala Val Glu Ile Arg Ser Arg His Ser Ser Tyr Pro Ala Gly Thr
 65                  70                  75                  80

Glu Asp Asp Glu Gly Met Gly Glu Glu Pro Ser Pro Phe Arg Gly Arg
                 85                  90                  95

Ser Arg Ser Ala Pro Pro Asn Leu Trp Ala Ala Gln Arg Tyr Gly Arg
                100                 105                 110

Glu Leu Arg Arg Met Ser Asp Glu Phe Val Asp Ser Phe Lys Lys Gly
            115                 120                 125

Leu Pro Arg Pro Lys Ser Ala Gly Thr Ala Thr Gln Met Arg Gln Ser
130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165
```

(2) INFORMATION FOR SEQ ID NO:2:

(i) SEQUENCE CHARACTERISTICS:
        (A) LENGTH: 1105 base pairs
        (B) TYPE: nucleic acid
        (C) STRANDEDNESS: single
        (D) TOPOLOGY: linear (vii) IMMEDIATE SOURCE:
        (A) LIBRARY: 358673
        (B) CLONE: SYNORAB01

(xi) SEQUENCE DESCRIPTION: SEQ ID NO:2:

```
CGACCGTCCG CGGGAGACTG AGGTCCTGAG CCGACAGCCT CAGCTCCCTG CCAGGCCAGA      60

CCCGGCAGAC AGATGAGGGC CCAGGAGGCC TGGCGGGCCT GGGGGCGCTA CGGTGGGAGA     120

GGAAGCCAGG GGTACCTGCC TCTGCCTTCC AGGGCCACCG TTGGCCCCAG CTGTGCCTTG     180

ACTACGTAAC ATCTTGTCCT CACAGCCCAG AGCATGTTCC AGATCCCAGA GTTTGAGCCG     240

AGTGAGCAGG AAGACTCCAG CTCTGCAGAG AGGGGCCTGG GCCCCAGCCC CGCAGGGGAC     300

GGGCCCTCAG GCTCCGGCAA GCATCATCGC CAGGCCCCAG GCCTCCTGTG GGACGCCAGT     360

CACCAGCAGG AGCAGCCAAC CAGCAGCAGC CATCATGGAG GCGCTGGGGC TGTGGAGATC     420

CGGAGTCGCC ACAGCTCCTA CCCCGCGGGG ACGGAGGACG ACGAAGGGAT GGGGGAGGAG     480

CCCAGCCCCT TTCGGGGCCG CTCGCGCTCG GCGCCCCCCA ACCTCTGGGC AGCACAGCGC     540

TATGGCCGCG AGCTCCGGAG GATGAGTGAC GAGTTTGTGG ACTCCTTTAA GAAGGGACTT     600

CCTCGCCCGA AGAGCGCGGG CACAGCAACG CAGATGCGGC AAAGCTCCAG CTGGACGCGA     660

GTCTTCCAGT CCTGGTGGGA TCGGAACTTG GGCAGGGGAA GCTCCGCCCC CTCCCAGTGA     720

CCTTCGCTCC ACATCCCGAA ACTCCACCCG TTCCCACTGC CCTGGGCAGC CATCTTGAAT     780

ATGGGCGGAA GTACTTCCCT CAGGCCTATG CAAAAAGAGG ATCCGTGCTG TCTCCTTTGG     840

AGGGAGGGCT GACCCAGATT CCCTTCCGGT GCGTGTGAAG CCACGGAAGG CTTGGTCCCA     900

TCGGAAGTTT TGGGTTTTCC GCCCACAGCC GCCGGAAGTG GCTCCGTGGC CCCGCCCTCA     960

GGCTCCGGGC TTTCCCCCAG GCGCCTGCGC TAAGTCGCGA GCCAGGTTTA ACCGTTGCGT    1020
```

```
CACCGGGACC CGAGCCCCCG CGATGCCCTG GGGGCCGTGC TCACTACCAA ATGTTAATAA      1080

AGCCCGCGTC TGTGCAAAAA AAAAA                                            1105
```

(2) INFORMATION FOR SEQ ID NO:3:

(i) SEQUENCE CHARACTERISTICS:
        (A) LENGTH: 440 amino acids
        (B) TYPE: amino acid
        (C) STRANDEDNESS: single
        (D) TOPOLOGY: linear (vii) IMMEDIATE SOURCE:
        (A) LIBRARY: LATRTUT02
        (B) CLONE: 1352286

(xi) SEQUENCE DESCRIPTION: SEQ ID NO:3:

```
Met Arg Val Val Thr Ile Val Ile Leu Leu Cys Phe Cys Lys Ala Ala
 1               5                  10                  15

Glu Leu Arg Lys Ala Ser Pro Gly Ser Val Arg Ser Arg Val Asn His
            20                  25                  30

Gly Arg Ala Gly Gly Gly Arg Arg Gly Ser Asn Pro Val Lys Arg Tyr
        35                  40                  45

Ala Pro Gly Leu Pro Cys Asp Val Tyr Thr Tyr Leu His Glu Lys Tyr
    50                  55                  60

Leu Asp Cys Gln Glu Arg Lys Leu Val Tyr Val Leu Pro Gly Trp Pro
65                  70                  75                  80

Gln Asp Leu Leu His Met Leu Leu Ala Arg Asn Lys Ile Arg Thr Leu
                85                  90                  95

Lys Asn Asn Met Phe Ser Lys Phe Lys Lys Leu Lys Ser Leu Asp Leu
            100                 105                 110

Gln Gln Asn Glu Ile Ser Lys Ile Glu Ser Glu Ala Phe Phe Gly Leu
        115                 120                 125

Asn Lys Leu Thr Thr Leu Leu Leu Gln His Asn Gln Ile Lys Val Leu
    130                 135                 140

Thr Glu Glu Val Phe Ile Tyr Thr Pro Leu Leu Ser Tyr Leu Arg Leu
145                 150                 155                 160

Tyr Asp Asn Pro Trp His Cys Thr Cys Glu Ile Glu Thr Leu Ile Ser
                165                 170                 175

Met Leu Gln Ile Pro Arg Asn Arg Asn Leu Gly Asn Tyr Ala Lys Cys
            180                 185                 190

Glu Ser Pro Gln Glu Gln Lys Asn Lys Lys Leu Arg Gln Ile Lys Ser
        195                 200                 205

Glu Gln Leu Cys Asn Glu Glu Lys Glu Gln Leu Asp Pro Lys Pro Gln
    210                 215                 220

Val Ser Gly Arg Pro Pro Val Ile Lys Pro Glu Val Asp Ser Thr Phe
225                 230                 235                 240

Cys His Asn Tyr Val Phe Pro Ile Gln Thr Leu Asp Cys Lys Arg Lys
                245                 250                 255

Glu Leu Lys Lys Val Pro Asn Asn Ile Pro Pro Asp Ile Val Lys Leu
            260                 265                 270

Asp Leu Ser Tyr Asn Lys Ile Asn Gln Leu Arg Pro Lys Glu Phe Glu
        275                 280                 285

Asp Val His Glu Leu Lys Lys Leu Asn Leu Ser Ser Asn Gly Ile Glu
    290                 295                 300

Phe Ile Asp Pro Ala Ala Phe Leu Gly Leu Thr His Leu Glu Glu Leu
305                 310                 315                 320
```

```
Asp Leu Ser Asn Asn Ser Leu Gln Asn Phe Asp Tyr Gly Val Leu Glu
            325                 330                 335

Asp Leu Tyr Phe Leu Lys Leu Leu Trp Leu Arg Asp Asn Pro Trp Arg
            340                 345                 350

Cys Asp Tyr Asn Ile His Tyr Leu Tyr Tyr Trp Leu Lys His His Tyr
            355                 360                 365

Asn Val His Phe Asn Gly Leu Glu Cys Lys Thr Pro Glu Glu Tyr Lys
        370                 375                 380

Gly Trp Ser Val Gly Lys Tyr Ile Arg Ser Tyr Glu Glu Cys Pro
385                 390                 395                 400

Lys Asp Lys Leu Pro Ala Tyr Pro Glu Ser Phe Asp Gln Asp Thr Glu
            405                 410                 415

Asp Asp Glu Trp Glu Lys Lys His Arg Asp His Thr Ala Lys Lys Gln
            420                 425                 430

Ser Val Ile Ile Thr Ile Val Gly
            435                 440

(2) INFORMATION FOR SEQ ID NO:4:

(i) SEQUENCE CHARACTERISTICS:
        (A) LENGTH: 2082 base pairs
        (B) TYPE: nucleic acid
        (C) STRANDEDNESS: single
        (D) TOPOLOGY: linear (vii) IMMEDIATE SOURCE:
        (A) LIBRARY: LATRTUT02
        (B) CLONE: 1352286

(xi) SEQUENCE DESCRIPTION: SEQ ID NO:4:

GAATGCAGCC CATTCTCTGG AGAACTTCCT CACACACCGC AGCAAAGAGA AGACTGAAAG      60

ACAAACCTGG GTGCAGCCAG AGAGGTCCAG ATAGATGAGC TTGTGGCATC CATTCCCCAA    120

GTTCAGCCTA GGGACTCCAC GTACCCCAGC TGGGTCTCAT TGTTCCAGAA CTGCATTAGT    180

TAAGATTACC CAGACTTGGA TTTCAAAGGA ATACTTTCAT TGTTCCGTCT GTAACACGAA    240

GTAATTGGGG CCAGCTGGAT GTCAGGATGC GTGTGGTTAC CATTGTAATC TTGCTCTGCT    300

TTTGCAAAGC GGCTGAGCTG CGCAAAGCAA GCCCAGGCAG TGTGAGAAGC CGAGTGAATC    360

ATGGCCGGGC GGGTGGAGGC GGAGAGGCT CCAACCCGGT CAAACGCTAC GCACCAGGCC    420

TCCCGTGTGA CGTGTACACA TATCTCCATG AGAAATACTT AGATTGTCAA GAAAGAAAAT    480

TAGTTTATGT GCTGCCTGGT TGGCCTCAGG ATTTGCTGCA CATGCTGCTA GCAAGAAACA    540

AGATCCGCAC ATTGAAGAAC AACATGTTTT CCAAGTTTAA AAAGCTGAAA AGCCTGGATC    600

TGCAGCAGAA TGAGATCTCT AAAATTGAGA GTGAGGCGTT CTTTGGTTTA AACAAACTCA    660

CCACCCTCTT ACTGCAGCAC AACCAGATCA AAGTCTTGAC GGAGGAAGTG TTCATTTACA    720

CACCTCTCTT GAGCTACCTG CGTCTTTATG ACAACCCCTG GCACTGTACT TGTGAGATAG    780

AAACGCTTAT TCAATGTTG CAGATTCCCA GGAACCGGAA TTTGGGGAAC TACGCCAAGT    840

GTGAAAGTCC ACAAGAACAA AAAATAAAA AACTGCGGCA GATAAAATCT GAACAGTTGT    900

GTAATGAAGA AAAGGAACAA TTGGACCCGA ACCCCAAGT GTCAGGGAGA CCCCCAGTCA    960

TCAAGCCTGA GGTGGACTCA ACTTTTTGCC ACAATTATGT GTTTCCCATA CAAACACTGG   1020

ACTGCAAAAG GAAAGAGTTG AAAAAAGTGC CAAACAACAT CCCTCCAGAT ATTGTTAAAC   1080

TTGACTTGTC ATACAATAAA ATCAACCAAC TTCGACCCAA GGAATTTGAA GATGTTCATG   1140

AGCTGAAGAA ATTAAACCTC AGCAGCAATG GCATTGAATT CATCGATCCT GCCGCTTTTT   1200
```

```
TAGGGCTCAC ACATTTAGAA GAATTAGATT TATCAAACAA CAGTCTGCAA AACTTTGACT    1260

ATGGCGTATT AGAAGACTTG TATTTTTTGA AACTCTTGTG GCTCAGAGAT AACCCTTGGA    1320

GATGTGACTA CAACATTCAC TACCTCTACT ACTGGTTAAA GCACCACTAC AATGTCCATT    1380

TTAATGGCCT GGAATGCAAA ACGCCTGAAG AATACAAAGG ATGGTCTGTG GGAAAATATA    1440

TTAGAAGTTA CTATGAAGAA TGCCCCAAAG ACAAGTTACC AGCATATCCT GAGTCATTTG    1500

ACCAAGACAC AGAAGATGAT GAATGGGAAA AAAAACATAG AGATCACACC GCAAAGAAGC    1560

AAAGCGTAAT AATTACTATA GTAGGATAAG GTAGAAATTG TTCTGATTGT AATTAGTTTT    1620

GTATTTTCTA TACTGGTGTT AGAAAACATA TGTTTACATT TGATTAACTG TGTTGCCTAT    1680

TTATGCAGGG TAATCCAGCT AAAGGAAGCT TTCTTTAATT ATAAGTATTA TTGTGACTAT    1740

TATAGTAATC AAGAGAATGC TATCATCCTG CTTGCCTGTC CATTTGTGGA ACAGCATCTG    1800

GTGATATGCA ATTCCACACT GGTAACCTGC AGCAGTTGGG TCCTAATGAT GGCATTAGAC    1860

TTTCATAATG TCCTGTATAA ATGTTTTTAC TGCTTTTAGA AAATAAAGAA AAAAAACTTG    1920

GTTCATGTTT ACATGCCTTT CGATAGCTGT TTGTGCATAC TTAAAGATGA TCAAAATGAT    1980

TTTATACAAA TGCTGTTATA ATAAAATGTC ATTCCCTACC CCTCTACTTT TTTTCAGTAA    2040

GTCATCTTAT ACATTAAATA AATTTCCATT TCTGAAAAAA AA                      2082
```

(2) INFORMATION FOR SEQ ID NO:5:

(i) SEQUENCE CHARACTERISTICS:
        (A) LENGTH: 469 amino acids
        (B) TYPE: amino acid
        (C) STRANDEDNESS: single
        (D) TOPOLOGY: linear (vii) IMMEDIATE SOURCE:
        (A) LIBRARY: OVARTUT01
        (B) CLONE: 815087

(xi) SEQUENCE DESCRIPTION: SEQ ID NO:5:

```
Met Asp Val Glu Asn Glu Gln Ile Leu Asn Val Asn Pro Ala Asp Pro
  1               5                  10                  15

Asp Asn Leu Ser Asp Ser Leu Phe Ser Gly Asp Glu Glu Asn Ala Gly
             20                  25                  30

Thr Glu Val Lys Asn Glu Ile Asn Gly Asn Trp Ile Ser Ala Ser
         35                  40                  45

Ser Ile Asn Glu Ala Arg Ile Asn Ala Lys Ala Lys Arg Arg Leu Arg
 50                  55                  60

Lys Asn Ser Ser Arg Asp Ser Gly Arg Gly Asp Ser Val Ser Asp Ser
 65                  70                  75                  80

Gly Ser Asp Ala Leu Arg Ser Gly Leu Thr Val Pro Thr Ser Pro Lys
                 85                  90                  95

Gly Arg Leu Leu Asp Arg Arg Ser Arg Ser Gly Lys Gly Arg Gly Leu
                100                 105                 110

Pro Lys Lys Gly Gly Ala Gly Gly Lys Gly Val Trp Gly Thr Pro Gly
            115                 120                 125

Gln Val Tyr Asp Val Glu Glu Val Asp Val Lys Asp Pro Asn Tyr Asp
        130                 135                 140

Asp Asp Gln Glu Asn Cys Val Tyr Glu Thr Val Leu Pro Leu Asp
145                 150                 155                 160

Glu Arg Ala Phe Glu Lys Thr Leu Thr Pro Ile Ile Gln Glu Tyr Phe
                165                 170                 175

Glu His Gly Asp Thr Asn Glu Val Ala Glu Met Leu Arg Asp Leu Asn
```

-continued

```
                    180                 185                 190
Leu Gly Glu Met Lys Ser Gly Val Pro Val Leu Ala Val Ser Leu Ala
                195                 200                 205
Leu Glu Gly Lys Ala Ser His Arg Glu Met Thr Ser Lys Leu Leu Ser
            210                 215                 220
Asp Leu Cys Gly Thr Val Met Ser Thr Thr Asp Val Glu Lys Ser Phe
225                 230                 235                 240
Asp Lys Leu Leu Lys Asp Leu Pro Glu Leu Ala Leu Asp Thr Pro Arg
                245                 250                 255
Ala Pro Gln Leu Val Gly Gln Phe Ile Ala Arg Ala Val Gly Asp Gly
                260                 265                 270
Ile Leu Cys Asn Thr Tyr Ile Asp Ser Tyr Lys Gly Thr Val Asp Cys
            275                 280                 285
Val Gln Ala Arg Ala Ala Leu Asp Lys Ala Thr Val Leu Leu Ser Met
        290                 295                 300
Ser Lys Gly Gly Lys Arg Lys Asp Ser Val Trp Gly Ser Gly Gly Gly
305                 310                 315                 320
Gln Gln Ser Val Asn His Leu Val Lys Glu Ile Asp Met Leu Leu Lys
                325                 330                 335
Glu Tyr Leu Leu Ser Gly Asp Ile Ser Glu Ala Glu His Cys Leu Lys
            340                 345                 350
Glu Leu Glu Val Pro His Phe His His Glu Leu Val Tyr Glu Ala Ile
        355                 360                 365
Ile Met Val Leu Glu Ser Thr Gly Glu Ser Thr Phe Lys Met Ile Leu
    370                 375                 380
Asp Leu Leu Lys Ser Leu Trp Lys Ser Ser Thr Ile Thr Val Asp Gln
385                 390                 395                 400
Met Lys Arg Gly Tyr Glu Arg Ile Tyr Asn Glu Ile Pro Asp Ile Asn
                405                 410                 415
Leu Asp Val Pro His Ser Tyr Ser Val Leu Glu Arg Phe Val Glu Glu
            420                 425                 430
Cys Phe Gln Ala Gly Ile Ile Ser Lys Gln Leu Arg Asp Leu Cys Pro
        435                 440                 445
Ser Arg Gly Arg Lys Arg Phe Val Ser Glu Gly Asp Gly Gly Arg Leu
    450                 455                 460
Lys Pro Glu Ser Tyr
465
```

(2) INFORMATION FOR SEQ ID NO:6:

(i) SEQUENCE CHARACTERISTICS:
        (A) LENGTH: 2395 base pairs
        (B) TYPE: nucleic acid
        (C) STRANDEDNESS: single
        (D) TOPOLOGY: linear (vii) IMMEDIATE SOURCE:
        (A) LIBRARY: OVARTUT01
        (B) CLONE: 815087

(xi) SEQUENCE DESCRIPTION: SEQ ID NO:6:

```
ACAGCTCGAG CTCGAGCCGC AAAACTGTCT GCAGACGTCA ATTTCGCCCC CCTCCCCCTT    60

GTGAGAACTC GCTACGTAGC CAGCAACTGT GTAGTGTCTA CAAATGATGA AAACGATCAG   120

AAATGCGATT AGGTGTCGGG GAAAAAGGG TTTCCCCTGT TTTTAACTTG TATTTTTACT    180

TTAATTGTTA CAATCTTGAT ATTCTTAACG TGACTTTTTT GGGAAACCAC CAAGTGCTTT   240
```

```
TTAAGCAAGG AGTTACTGAT TCTGAAGGAA GATTTCCATT AGGTAATTTG TTTAATCAGT      300

GCAAGCGAAA TTAAGGGAAA ATGGATGTAG AAAATGAGCA GATACTGAAT GTAAACCCTG      360

CAGATCCTGA TAACTTAAGT GACTCTCTCT TTTCCGGTGA TGAAGAAAAT GCTGGGACTG      420

AGGAAGTAAA GAATGAAATA AATGGAAATT GGATTTCAGC ATCCTCCATT AACGAAGCTA      480

GAATTAATGC CAAGGCAAAA AGGCGACTAA GGAAAAACTC ATCCCGGGAC TCTGGCAGAG      540

GCGATTCGGT CAGCGACAGT GGGAGTGACG CCCTTAGAAG TGGATTAACT GTGCCAACCA      600

GTCCAAAGGG AAGGTTGCTG GATAGGCGAT CCAGATCTGG GAAAGGAAGG GGACTACCAA      660

AGAAAGGTGG TGCAGGAGGC AAAGGTGTCT GGGGTACACC TGGACAGGTG TATGATGTGG      720

AGGAGGTGGA TGTGAAAGAT CCTAACTATG ATGATGACCA GGAGAACTGT GTTTATGAAA      780

CTGTAGTTTT GCCTTTGGAT GAAAGGGCAT TTGAGAAGAC TTTAACACCA ATCATACAGG      840

AATATTTTGA GCATGGAGAT ACTAATGAAG TTGCGGAAAT GTTAAGAGAT TTAAATCTTG      900

GTGAAATGAA AAGTGGAGTA CCAGTGTTGG CAGTATCCTT AGCATTGGAG GGAAGGCTA      960

GTCATAGAGA GATGACATCT AAGCTTCTTT CTGACCTTTG TGGGACAGTA ATGAGCACAA     1020

CTGATGTGGA AAAATCATTT GATAAATTGT TGAAAGATCT ACCTGAATTA GCACTGGATA     1080

CTCCTAGAGC ACCACAGTTG GTGGGCCAGT TTATTGCTAG AGCTGTTGGA GATGGAATTT     1140

TATGTAATAC CTATATTGAT AGTTACAAAG GAACTGTAGA TTGTGTGCAG GCTAGAGCTG     1200

CTCTGGATAA GGCTACCGTG CTTCTGAGTA TGTCTAAAGG TGGAAAGCGT AAAGATAGTG     1260

TGTGGGGCTC TGGAGGTGGG CAGCAATCTG TCAATCACCT TGTTAAAGAG ATTGATATGC     1320

TGCTGAAAGA ATATTTACTC TCTGGAGACA TATCTGAAGC TGAACATTGC CTTAAGGAAC     1380

TGGAAGTACC TCATTTTCAC CATGAGCTTG TATATGAAGC TATTATAATG GTTTTAGAGT     1440

CAACTGGAGA AAGTACATTT AAGATGATTT TGGATTTATT AAAGTCCCTT TGGAAGTCTT     1500

CTACCATTAC TGTAGACCAA ATGAAAAGAG GTTATGAGAG AATTTACAAT GAAATTCCGG     1560

ACATTAATCT GGATGTCCCA CATTCATACT CTGTGCTGGA GCGGTTTGTA GAAGAATGTT     1620

TTCAGGCTGG AATAATTTCC AAACAACTCA GAGATCTTTG TCCTTCAAGG GGCAGAAAGC     1680

GTTTTGTAAG CGAAGGAGAT GGAGGTCGTC TTAAACCAGA GAGCTACTGA ATATAAGAAC     1740

TCTTGCAGTC TTAGATGTTA TAAAAATATA TATCTGAATT GTAAGAGTTG TTAGCACAAG     1800

TTTTTTTTTT TTTTTTTTTT TAAGCACTTG TTTTGGGTAC AAGGCATTTC TGACATTTTA     1860

TAAACCTACA TTTAAGGGGA ATTTTTAAAG GAAATGTTTT TTCTTTTTTT TTTGTTTTTC     1920

GAGGGGGCAA GGAGGGACAG AAAAGTAACC TCTTCTTAAG TGGAATATTC TAATAAGCTA     1980

CCTTTTGTAA GTGCCATGTT TATTATCTAA TCATTCCAAG TTTTGCATTG ATGTCTGACT     2040

GCCACTCCTT TCTTTCAAGG ACAGTGTTTT TTGTAGTAAA ATCACTGGTT TATACAAAGC     2100

TTTATTTAGG GGGTAAAGTT AAGCTGCTAA AACCCCATGT TGGCTGCTGC TGTTGAGATA     2160

CTGTGCTTTG GGAGTAAAAA AAGAAGTTA TTTCTTTGTC TTAAAGAATT TTTAAAAAAT      2220

TAGTCATGAG ACTTATTCAT CTTTCCAGGG AACATACTGA TTGGTCTTAA AAGACTAGAC     2280

AGTTAAGTAA AAGGTGGCTG GAACATCTAT TTTTCTACAA AACTGGAAAA ATGAACCTGG     2340

TTCTAGAAGA ATGTACACCA AAATAAAACA TGTGAAGCAG TATTGAAAAA AAAAA          2395
```

(2) INFORMATION FOR SEQ ID NO:7:

(i) SEQUENCE CHARACTERISTICS:
        (A) LENGTH: 168 amino acids
        (B) TYPE: amino acid
        (C) STRANDEDNESS: single (D) TOPOLOGY: linear (vii) IMMEDIATE SOURCE:
    (A) LIBRARY: GenBank
    (B) CLONE: 1683637

(xi) SEQUENCE DESCRIPTION: SEQ ID NO:7:

```
Met Phe Gln Ile Pro Glu Phe Glu Pro Ser Glu Gln Glu Asp Ser Ser
 1               5                  10                  15

Ser Ala Glu Arg Gly Leu Gly Pro Ser Pro Ala Gly Asp Gly Pro Ser
                20                  25                  30

Gly Ser Gly Lys His His Arg Gln Ala Pro Gly Leu Leu Trp Asp Ala
            35                  40                  45

Ser His Gln Gln Glu Gln Pro Thr Ser Ser Ser His His Gly Gly Arg
50                  55                  60

Trp Gly Cys Gly Asp Pro Glu Ser Pro Gln Leu Leu Pro Arg Gly Asp
65                  70                  75                  80

Gly Gly Arg Arg Arg Asp Gly Gly Gly Ala Gln Pro Phe Arg Gly Arg
                85                  90                  95

Ser Arg Ser Ala Pro Pro Asn Leu Trp Ala Ala Gln Arg Tyr Gly Arg
                100                 105                 110

Glu Leu Arg Arg Met Ser Asp Glu Phe Val Asp Ser Phe Lys Lys Gly
            115                 120                 125

Leu Pro Arg Pro Lys Ser Ala Gly Thr Ala Thr Gln Met Arg Gln Ser
130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165
```

(2) INFORMATION FOR SEQ ID NO:8:

(i) SEQUENCE CHARACTERISTICS:
        (A) LENGTH: 313 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1236329

(xi) SEQUENCE DESCRIPTION: SEQ ID NO:8:

```
Met Arg Val Val Thr Ile Val Ile Leu Leu Cys Phe Cys Lys Ala Ala
 1               5                  10                  15

Glu Leu Arg Lys Ala Ser Pro Gly Ser Val Arg Ser Arg Val Asn His
                20                  25                  30

Gly Arg Ala Gly Gly Gly Arg Arg Gly Ser Asn Pro Val Lys Arg Tyr
            35                  40                  45

Ala Pro Gly Leu Pro Cys Asp Val Tyr Thr Tyr Leu His Glu Lys Tyr
50                  55                  60

Leu Asp Cys Gln Glu Arg Lys Leu Val Tyr Val Leu Pro Gly Trp Pro
65                  70                  75                  80

Gln Asp Leu Leu His Met Leu Leu Ala Arg Asn Lys Ile Arg Thr Leu
                85                  90                  95

Lys Asn Asn Met Phe Ser Lys Phe Lys Lys Leu Lys Ser Leu Asp Leu
                100                 105                 110

Gln Gln Asn Glu Ile Ser Lys Ile Glu Ser Glu Ala Phe Phe Gly Leu
            115                 120                 125
```

```
Asn Lys Leu Thr Thr Leu Leu Leu Gln His Asn Gln Ile Lys Val Leu
    130                 135                 140

Thr Glu Glu Val Phe Ile Tyr Thr Pro Leu Leu Ser Tyr Leu Arg Leu
145                 150                 155                 160

Tyr Asp Asn Pro Trp His Cys Thr Cys Glu Ile Glu Thr Leu Ile Ser
                165                 170                 175

Met Leu Gln Ile Pro Arg Asn Arg Asn Leu Ala Asn Tyr Ala Lys Cys
                180                 185                 190

Glu Ser Pro Gln Glu Gln Lys Asn Lys Leu Arg Gln Ile Lys Ser
            195                 200                 205

Glu Gln Leu Cys Asn Glu Glu Lys Glu Gln Leu Asp Pro Lys Pro
    210                 215                 220

Gln Val Ser Gly Arg Pro Val Ile Lys Pro Glu Val Asp Ser Thr
225                 230                 235                 240

Phe Cys His Asn Tyr Val Phe Pro Ile Gln Thr Leu Asp Cys Lys Arg
                245                 250                 255

Lys Glu Leu Lys Lys Val Pro Asn Asn Ile Pro Pro Asp Ile Val Lys
                260                 265                 270

Leu Asp Leu Ser Tyr Asn Lys Ile Asn Gln Leu Arg Pro Lys Glu Phe
                275                 280                 285

Glu Asp Val His Glu Leu Lys Lys Leu Asn Leu Ser Ser Asn Gly Ile
    290                 295                 300

Glu Phe Ile Asp Pro Gly Ser Leu Arg
305                 310

(2) INFORMATION FOR SEQ ID NO:9:

(i) SEQUENCE CHARACTERISTICS:
        (A) LENGTH: 469 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1384078

(xi) SEQUENCE DESCRIPTION: SEQ ID NO:9:

Met Asp Ile Glu Asn Glu Gln Thr Leu Asn Val Asn Pro Thr Asp Pro
1               5                   10                  15

Asp Asn Leu Ser Asp Ser Leu Phe Ser Gly Asp Glu Glu Asn Ala Gly
                20                  25                  30

Thr Glu Glu Ile Lys Asn Glu Ile Asn Gly Asn Trp Ile Ser Ala Ser
            35                  40                  45

Thr Ile Asn Glu Ala Arg Ile Asn Ala Lys Ala Lys Arg Arg Leu Arg
50                  55                  60

Lys Asn Ser Ser Arg Asp Ser Gly Arg Gly Asp Ser Val Ser Asp Asn
65                  70                  75                  80

Gly Ser Glu Ala Val Arg Ser Gly Val Ala Val Pro Thr Ser Pro Lys
                85                  90                  95

Gly Arg Leu Leu Asp Arg Arg Ser Arg Ser Gly Lys Gly Arg Gly Leu
                100                 105                 110

Pro Lys Lys Gly Gly Ala Gly Gly Lys Gly Val Trp Gly Thr Pro Gly
            115                 120                 125

Gln Val Tyr Asp Val Glu Glu Val Asp Val Lys Asp Pro Asn Tyr Asp
    130                 135                 140
```

-continued

```
Asp Asp Gln Glu Asn Cys Val Tyr Glu Thr Val Val Leu Pro Leu Asp
145                 150                 155                 160

Glu Thr Ala Phe Glu Lys Thr Leu Thr Pro Ile Ile Gln Glu Tyr Phe
                165                 170                 175

Glu His Gly Asp Thr Asn Glu Val Ala Glu Met Leu Arg Asp Leu Asn
                180                 185                 190

Leu Gly Glu Met Lys Ser Gly Val Pro Val Leu Ala Val Ser Leu Ala
            195                 200                 205

Leu Glu Gly Lys Ala Ser His Arg Glu Met Thr Ser Lys Leu Leu Ser
        210                 215                 220

Asp Leu Cys Gly Thr Val Met Ser Thr Asn Asp Val Glu Lys Ser Phe
225                 230                 235                 240

Asp Lys Leu Leu Lys Asp Leu Pro Glu Leu Ala Leu Asp Thr Pro Arg
                245                 250                 255

Ala Pro Gln Leu Val Gly Gln Phe Ile Ala Arg Ala Val Gly Asp Gly
                260                 265                 270

Ile Leu Cys Asn Thr Tyr Ile Asp Ser Tyr Lys Gly Thr Val Asp Cys
            275                 280                 285

Val Gln Ala Arg Ala Ala Leu Asp Lys Ala Thr Val Leu Leu Ser Met
        290                 295                 300

Ser Lys Gly Gly Lys Arg Lys Asp Ser Val Trp Gly Ser Gly Gly Gly
305                 310                 315                 320

Gln Gln Pro Val Asn His Leu Val Lys Glu Ile Asp Met Leu Leu Lys
                325                 330                 335

Glu Tyr Leu Leu Ser Gly Asp Ile Ser Glu Ala Glu His Cys Leu Lys
            340                 345                 350

Glu Leu Glu Val Pro His Phe His His Glu Leu Val Tyr Glu Ala Ile
        355                 360                 365

Val Met Val Leu Glu Ser Thr Gly Glu Ser Ala Phe Lys Met Ile Leu
    370                 375                 380

Asp Leu Leu Lys Ser Leu Trp Lys Ser Ser Thr Ile Thr Ile Asp Gln
385                 390                 395                 400

Met Lys Arg Gly Tyr Glu Arg Ile Tyr Asn Glu Ile Pro Asp Ile Asn
                405                 410                 415

Leu Asp Val Pro His Ser Tyr Ser Val Leu Glu Arg Phe Val Glu Glu
                420                 425                 430

Cys Phe Gln Ala Gly Ile Ile Ser Lys Gln Leu Arg Asp Leu Cys Pro
            435                 440                 445

Ser Arg Gly Arg Lys Arg Phe Val Ser Glu Gly Asp Gly Gly Arg Leu
        450                 455                 460

Lys Pro Glu Ser Tyr
465
```

What is claimed is:

1. A purified polypeptide comprising an amino acid sequence selected from the group consisting of:
   a) SEQ ID NO:3, SEQ ID NO:5, and
   b) a fragment of SEQ ID NO:3 consisting of at least fifteen contiguous amino acid residues from about amino acid residue A309 to about amino acid residue G440 of SEQ ID NO:3.

2. A purified protein associated with apoptosis having at least 90% amino acid identity over the complete sequence of the amino acid sequence of SEQ ID NO:3 or SEQ ID NO:5, and which possesses apoptosis activity.

3. A composition comprising the polypeptide of claim 1 in conjunction with a suitable pharmaceutical carrier.

4. A method for using a protein to screen a plurality of other molecules or compounds for a molecule or compound which specifically binds the protein, the method comprising:
   (a) combining the protein of claim 1 with the molecules or compounds under conditions suitable to allow complex formation, and
   (b) detecting complex formation, wherein the presence of the complex identifies a molecule or compound which specifically binds the protein.

5. The method of claim 4, wherein the molecule or compound is selected from the group consisting of inhibitors, peptides, antibodies, immunoglogulins, and pharmaceutical agents.

6. A method for screening a compound for effectiveness as an agonist of a polypeptide of claim 1, possessing apoptotic activity the method comprising:
   a) exposing a sample comprising a polypeptide of claim 1 to a compound, and
   b) detecting an agonist of apoptotic activity in the sample.

7. A method for screening a compound for effectiveness as an antagonist of a polypeptide of claim 1, possessing apoptotic activity the method comprising:
   a) exposing a sample comprising a polypeptide of claim 1 to a compound, and
   b) detecting an antagonist apoptotic activity in the sample.

8. A method of using a protein or a fragment thereof to purify a molecule or compound which specifically binds the protein from a sample, the method comprising:
   a) combining the protein or a fragment thereof of claim 1 with a sample under conditions to allow specific binding;
   b) recovering the bound protein; and
   d) separating the protein from the molecule or compound, thereby obtaining purified molecule or compound.

* * * * *